US010996183B2

(12) United States Patent
Iwata et al.

(10) Patent No.: US 10,996,183 B2
(45) Date of Patent: May 4, 2021

(54) DETECTION DEVICE AND METHOD OF CONTROLLING DETECTION DEVICE

(71) Applicant: SHARP KABUSHIKI KAISHA, Osaka (JP)

(72) Inventors: Noboru Iwata, Sakai (JP); Tatsuhito Arimura, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 146 days.

(21) Appl. No.: 16/319,449

(22) PCT Filed: May 23, 2017

(86) PCT No.: PCT/JP2017/019203
§ 371 (c)(1),
(2) Date: Jan. 21, 2019

(87) PCT Pub. No.: WO2018/016170
PCT Pub. Date: Jan. 25, 2018

(65) Prior Publication Data
US 2019/0293591 A1      Sep. 26, 2019

(30) Foreign Application Priority Data
Jul. 22, 2016    (JP) .............................. JP2016-144914

(51) Int. Cl.
*G01N 27/22*        (2006.01)

(52) U.S. Cl.
CPC .......... *G01N 27/223* (2013.01); *G01N 27/22* (2013.01); *G01N 27/226* (2013.01); *G01N 27/228* (2013.01)

(58) Field of Classification Search
CPC .... G01N 27/223; G01N 27/22; G01N 27/226; G01N 27/228
USPC ........................................ 324/514, 658–665
See application file for complete search history.

(56) References Cited

U.S. PATENT DOCUMENTS

| 4,571,543 A | * | 2/1986 | Raymond | ............ | G01N 27/227 257/414 |
| 5,304,937 A | * | 4/1994 | Meyer | .................. | G01D 5/2415 324/662 |
| 5,394,096 A | * | 2/1995 | Meyer | .................. | G01D 5/2415 324/662 |

(Continued)

FOREIGN PATENT DOCUMENTS

| JP | S59-230153 A | 12/1984 |
| JP | H01-300963 A | 12/1989 |

(Continued)

*Primary Examiner* — Patrick Assouad
*Assistant Examiner* — Sean Curtis
(74) *Attorney, Agent, or Firm* — ScienBiziP, P.C.

(57) ABSTRACT

A detection device includes a plurality of detection units formed on a semiconductor circuit, a correction capacitive element that indicates a correction capacitance value for correcting detected capacitance values detected by the detection units, a difference acquisition circuit that acquires a difference value between each of the detected capacitance values and the correction capacitance value, and a conversion circuit that converts the difference value into a digital signal. The correction capacitive element, the difference acquisition circuit, and the conversion circuit are formed on the semiconductor circuit.

13 Claims, 24 Drawing Sheets

(56) References Cited

U.S. PATENT DOCUMENTS

| | | | | |
|---|---|---|---|---|
| 7,208,961 B2* | 4/2007 | Miyasaka | ............ | G06K 9/0002 324/658 |
| 7,222,531 B2* | 5/2007 | Isogai | ................ | G01N 27/223 73/335.02 |
| 7,267,002 B2* | 9/2007 | Itakura | .................... | G01D 5/24 324/670 |
| 7,387,024 B2* | 6/2008 | Itakura | ................ | G01N 27/223 73/335.04 |
| 8,188,754 B2* | 5/2012 | Teterwak | ................ | G01D 5/24 324/681 |
| 8,357,958 B2* | 1/2013 | Cummins | ............ | G01N 27/223 257/253 |
| 8,471,304 B2* | 6/2013 | Fedder | ................ | G01N 27/226 257/252 |
| 8,779,781 B2* | 7/2014 | Nguyen | ............... | G01N 27/226 324/679 |
| 8,823,396 B2* | 9/2014 | Astley | .................... | G01R 27/02 324/660 |
| 8,852,983 B1* | 10/2014 | Fedder | ................ | G01N 27/226 438/49 |
| 9,151,640 B2* | 10/2015 | Teterwak | ................ | G01D 5/24 |
| 9,287,219 B2* | 3/2016 | Del Signore | ........ | H01L 23/552 |
| 9,459,298 B2* | 10/2016 | Teterwak | ............ | G01R 27/2605 |
| 9,493,338 B2* | 11/2016 | Nakagawa | ................ | G01L 9/12 |
| 9,738,508 B2* | 8/2017 | Hong | ................ | G01L 9/00 |
| 10,186,479 B2* | 1/2019 | Katsumura | ............ | H01L 28/65 |
| 10,502,702 B2* | 12/2019 | Hong | ................ | G01N 27/223 |
| 10,718,730 B2* | 7/2020 | Ashida | ............... | G01R 27/2623 |
| 2005/0188764 A1* | 9/2005 | Itakura | ................ | G01N 27/223 73/335.04 |
| 2006/0037393 A1* | 2/2006 | Itakura | ................ | G01N 27/223 73/335.04 |
| 2006/0076963 A1* | 4/2006 | Miyasaka | ............ | G06K 9/0002 324/662 |
| 2008/0238449 A1* | 10/2008 | Shizu | .................... | G01N 27/226 324/689 |
| 2011/0012618 A1* | 1/2011 | Teterwak | ............. | G01D 5/2417 324/607 |
| 2011/0316054 A1* | 12/2011 | Fedder | ...................... | C23F 1/20 257/253 |
| 2012/0235784 A1* | 9/2012 | Teterwak | ........... | G01R 27/2605 340/5.6 |
| 2012/0256645 A1* | 10/2012 | Nguyen | ............... | G01N 27/223 324/679 |
| 2014/0026653 A1* | 1/2014 | Del Signore | ........ | G01N 27/223 73/335.04 |
| 2014/0197500 A1* | 7/2014 | Guillemet | ............ | G01N 27/226 257/414 |
| 2014/0197851 A1* | 7/2014 | Astley | ................ | G01N 33/0062 324/660 |
| 2014/0295605 A1* | 10/2014 | Fedder | ...................... | C23F 1/20 438/49 |
| 2014/0367811 A1* | 12/2014 | Nakagawa | ............. | H04R 31/00 257/416 |
| 2015/0008543 A1* | 1/2015 | Hong | .................... | B81B 3/0059 257/417 |
| 2015/0233989 A1* | 8/2015 | Chou | ................ | G01R 27/2605 345/174 |
| 2016/0003758 A1* | 1/2016 | Hong | .................... | G01N 27/223 324/664 |
| 2016/0025786 A1* | 1/2016 | Teterwak | ........... | G01R 27/2605 324/681 |
| 2018/0059052 A1* | 3/2018 | Hoque | .................... | H01L 29/93 |
| 2019/0041349 A1* | 2/2019 | Suy | ........ | G01N 27/226 |
| 2019/0293591 A1* | 9/2019 | Iwata | ............ | G01N 27/228 |
| 2020/0158676 A1* | 5/2020 | Inoue | .................. | G01N 27/226 |

FOREIGN PATENT DOCUMENTS

| | | |
|---|---|---|
| JP | 2012-145384 A | 8/2012 |
| JP | 2016-504595 A | 2/2016 |

* cited by examiner

DETECTION DEVICE AND METHOD OF CONTROLLING DETECTION DEVICE

TECHNICAL FIELD

The present disclosure relates to a detection device that detects a detection target based on a change in capacitance, and to a method of controlling the detection device.

BACKGROUND ART

Detection devices that detect a detection target such as gas and liquid include a device that detects a change in capacitance due to contact with the detection target.

For example, PTL 1 discloses an anesthesia sensor including: a temperature/humidity sensitive element that is sensitive to temperature/humidity but is not sensitive to anesthetic gas; and an anesthesia sensitive element that is sensitive to anesthetic gas and temperature/humidity. The anesthesia sensor performs calibration with an amount of change in the capacitance of the anesthesia sensitive element with respect to temperature/humidity offset by an amount of change in the capacitance of the temperature/humidity sensitive element with respect to the temperature/humidity.

PTL 2 discloses a capacitance detection device that detects the existence of a certain nonaqueous material in a fluid. This device includes a plurality of interdigit capacitors (comb-shaped electrodes), and the type of gas to be detected is determined by comparing outputs from different capacitors.

The anesthesia sensor disclosed in PTL 1 is difficult to downsize because the sensitive elements are formed separately from an electric circuit. Downsizing of the sensitive elements leads to sensitive elements with a smaller area and thus lowers detection sensitivity, making it difficult to detect low concentration gas. The device disclosed in PTL 2 is difficult to downsize because a substrate on which the capacitors are mounted and an electronic circuit that detects a change in the capacitance of the capacitor are separately provided.

Meanwhile, PTL 3 discloses a sensor with a flat-plate capacitive gas sensor assembled on a semiconductor circuit (Application-Specific Integrated Circuits (ASIC)). One object of the technique disclosed in PTL 3 is to downsize the sensor.

CITATION LIST

Patent Literature

PTL 1: JP H1-300963 A (published on Dec. 5, 1989)
PTL 2: JP S59-230153 A (published on Dec. 24, 1984)
PTL 3: JP 2016-504595 T (published on Feb. 12, 2016)

SUMMARY OF DISCLOSURE

Technical Problem

With the sensor disclosed in PTL 3, which has the configuration featuring a single sensor element (the flat-plate capacitive gas sensor) assembled on the semiconductor circuit, it is impossible to identify the detection target using a plurality of sensor elements with high sensitivity.

Generally, the reduction in the area of the detection unit due to the downsizing of the detection device results in a lower signal intensity of the detection signal (a smaller capacitance change amount). Furthermore, when a detection target at a low concentration is to be detected, the intensity of the detection signal is lower than the capacitance value of the detection material itself by several digits, and thus the detection signal is difficult to acquire with high resolution. None of PTLs 1 to 3 disclose a method suitable for detection requiring such high resolution.

The present disclosure is made in view of the above, and an object of the present disclosure is to implement a small yet highly sensitive detection device.

Solution to Problem

To achieve the object describe above, a detection device according to an aspect of the present disclosure includes a plurality of detection units each formed on a semiconductor circuit and including a detection layer that includes a capacitance value varying when the detection layer comes into contact with a detection target, a correction capacitive element that indicates a correction capacitance value for correcting detected capacitance values detected by the detection units, a difference acquisition circuit that acquires a difference value between each of the detected capacitance values and the correction capacitance value, and a conversion circuit that converts the difference value into a digital signal. The correction capacitive element, the difference acquisition circuit, and the conversion circuit are formed on the semiconductor circuit.

To achieve the object describe above, a method of controlling a detection device according to an aspect of the present disclosure is a method of controlling a detection device that detects a detection target based on a change in capacitance. The detection device includes a plurality of detection units each formed on a semiconductor circuit and includes a detection layer that includes a capacitance value varying when the detection layer comes into contact with a detection target, a correction capacitive element that indicates a correction capacitance value for correcting detected capacitance values detected by the detection units, a difference acquisition circuit that acquires a difference value between each of the detected capacitance values and the correction capacitance value, and a conversion circuit that converts the difference value into a digital signal. The correction capacitive element, the difference acquisition circuit, and the conversion circuit are formed on the semiconductor circuit. The correction capacitive element is a variable capacitive element the correction capacitance value of which is variable. The method of controlling the detection device includes capacitance value setting step of setting the correction capacitance value in accordance with the difference values obtained by the difference acquisition circuit.

Advantageous Effects of Disclosure

The detection device according to an aspect of the present disclosure provides an advantageous effect of implementing a small yet highly sensitive detection device.

The method of controlling a detection device according to an aspect of the present disclosure provides an advantageous effect of performing particularly highly sensitive detection.

DESCRIPTION OF EMBODIMENTS

First Embodiment

Figure 1:
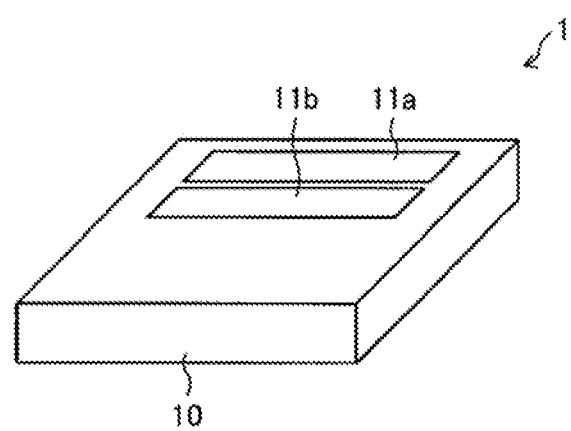
FIG. 1 is a perspective view illustrating a configuration of an outer appearance of a detection device according to a first embodiment of the present disclosure.
Figure 2A:
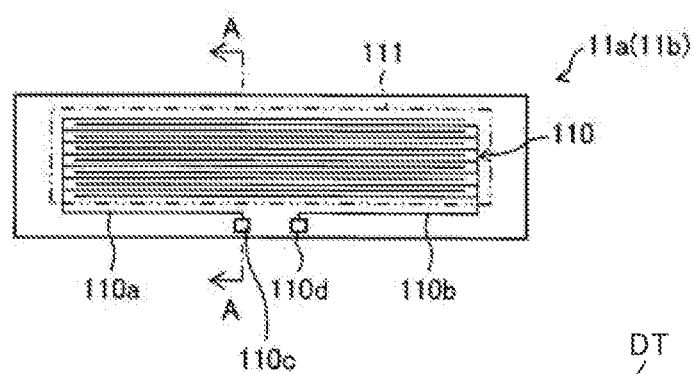
FIG. 2A is an upper view illustrating detection units of the detection device illustrated in FIG. 1.
Figure 2B:
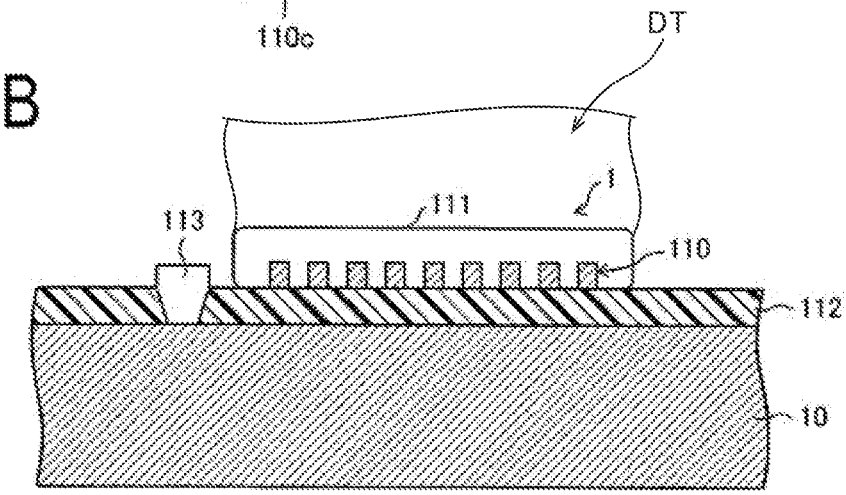
FIG. 2B is a cross-sectional view taken along line A-A in FIG. 2A.

A first embodiment of the present disclosure will be described using FIGS. 1 to 4. First of all, an overview of a detection device 1 according to the first embodiment will be described with reference to FIGS. 1 to 3. FIG. 1 is a perspective view illustrating a configuration of an outer appearance of the detection device 1. FIG. 2A is an upper view illustrating detection units 11a and 11b of the detection device 1, and FIG. 2B is a cross-sectional view taken along line A-A in FIG. 2A.

As illustrated in FIG. 1, the detection device 1 includes a semiconductor circuit 10. The two detection units 11a and 11b are arranged side by side on the semiconductor circuit 10. As illustrated in FIGS. 2A and 2B, the detection units 11a and 11b each have a rectangular shape, and include a comb-shaped electrode 110 and a detection layer 111.

The comb-shaped electrode 110 are formed to be in a planer shape on the semiconductor circuit 10 with an insulating layer 112 interposed therebetween. The comb-shaped electrode 110 is made by combining a first electrode 110a and a second electrode 110b made of a conductive material. The first electrode 110a and the second electrode 110b each have a comb shape, and one comb-tooth part of one of the electrodes is disposed between two adjacent ones of comb-tooth parts of the other one of the electrodes, without coming into contact with each other. Thus, the comb-tooth parts of the first electrode 110a and the comb-tooth parts of the second electrode 110b are alternately arranged.

The first electrode 110a and the second electrode 110b respectively have a terminal 110c and a terminal 110d each electrically connected with the semiconductor circuit 10 through a via hole 113. A protection film made of metal or semiconductor oxide or nitride may be formed on the comb-shaped electrode 110. The via hole 113 may be filled with a conductive matter.

The material forming the comb-shaped electrode 110 is composed mainly of a highly conductive metal, such as aluminum, copper, gold, silver, titanium, indium, and tin, and is any of these metals used singly, an alloy of these metals or with other metals, or a conductive oxide such as indium tin oxide.

The detection layer 111 is formed to be disposed at least between the comb-tooth parts of the first electrode 110a and the comb-tooth parts of the second electrode 110b in the comb-shaped electrode 110, and may be formed to cover portions where the comb-tooth parts of the first electrode 110a and the comb-tooth parts of the second electrode 110b are arranged.

The detection layer 111 may be formed of any dielectric material as long as the capacitance value of the comb-shaped electrode 110 changes when the detection layer 111 comes into contact with a detection target DT, and is not limited to a particular material. For example, organic compounds, metal or semiconductor oxides, nitrides, carbides, metal complexes, and the like are applicable as the material of the detection layer 111. Examples of the material of the detection layer 111 may include materials obtained by adding metal fine particles having modification groups or catalytic activity, dopants, or antibodies for causing antigen-antibody reactions to any of the above-described materials.

Specific examples of the material of the detection layer 111 may include various types of polymers and metal complexes in which an organic compound, such as phthalocyanine or porphyrin, is modified with a metal element. The above-described metal or semiconductor oxides, nitrides, and carbides include tin oxide, titanium oxide, silicon oxide, silicon nitride, silicon carbide, barium titanate, and lead zirconate titanate. These materials may be turned into a porous body.

The detection layer 111 is formed with a film of such a material formed on the comb-shaped electrode 110 by a coating or film formation method such as spin coating, inkjet printing, screen printing, aerosol deposition, vacuum deposition, sputtering, and photolithography. The film of the material thus coated or formed on the comb-shaped electrode 110 may be heated to be calcined.

The detection layer 111 has a dielectric constant changing when components in gas or liquid as the detection target DT are absorbed or adsorbed in or on the detection layer 111, or cause a redox reaction with the detection layer 111.

The comb-shaped electrode 110 has a capacitance value changing in accordance with the change in the dielectric constant of the detection layer 111. Thus, the comb-shaped electrode 110 is configured to have a capacitance value changing when the detection target DT comes into contact with the detection units 11a and 11b of the detection layer 111. The detection device 1 uses the semiconductor circuit 10 to electrically detect such a change in the capacitance value of the comb-shaped electrode 110.

The detection target DT detected by the detection units 11a and 11b is components in a plurality of different types of gas components and liquid. Thus, the detection layers 111 of the detection units 11a and 11b are made of different materials so that the detection units 11a and 11b provide different responses, that is, response patterns different from each other in the amount of change in the capacitance values.

The different materials may be materials different from each other in the main component, or may be materials with the same main material or structure and with different additional materials such as modifying groups and fine metal particles.

The detection target DT is not limited to particular types, and examples of the detection target DT that are gas components include oxidizing/reducing gas, combustible gas, and Volatile Organic Compounds (VOC) gas. Specific examples of the detection target DT include nitrogen oxides, sulfur oxides, carbon monoxide, carbon dioxide, water vapor, hydrogen, methane, ethane, ethylene, propane, butane, methanol, ethanol, isopropyl alcohol, ammonia, formaldehyde, acetaldehyde, acetone, chloroform, isobutane, hydrocarbon, and other gases. Examples of the detection target DT that are liquid components include organic solvents, acid/basic liquid, liquid-containing metal, and protein and the like.

Figure 3:
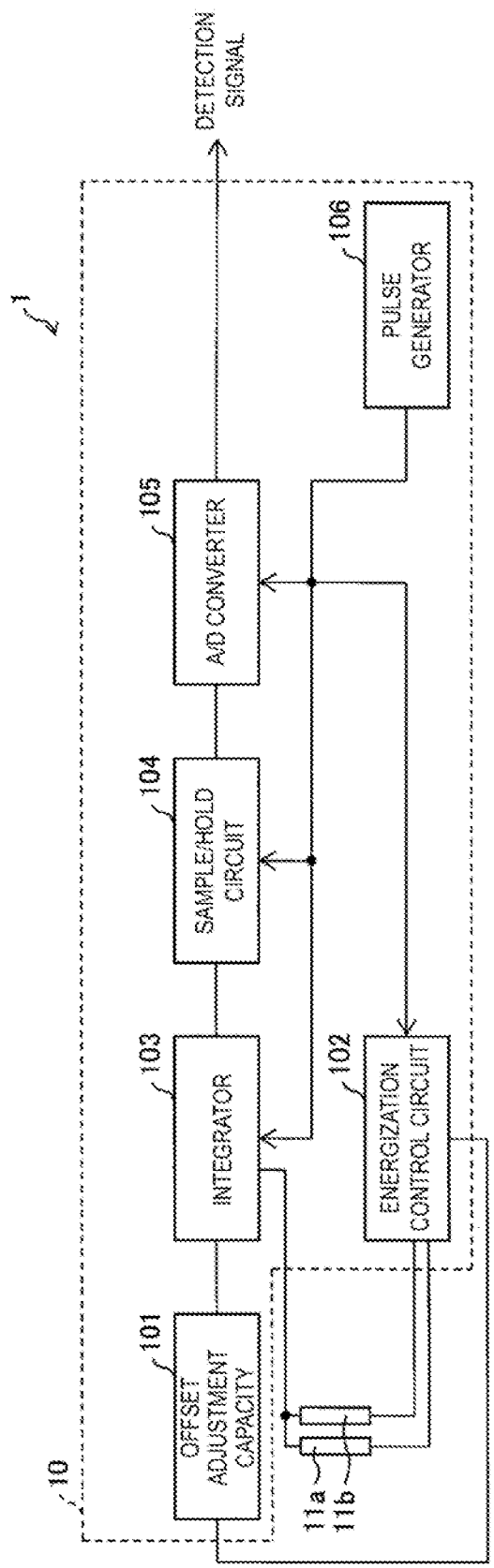
FIG. 3 is a block diagram illustrating a circuit configuration of the detection device illustrated in FIG. 1.
Figure 4:
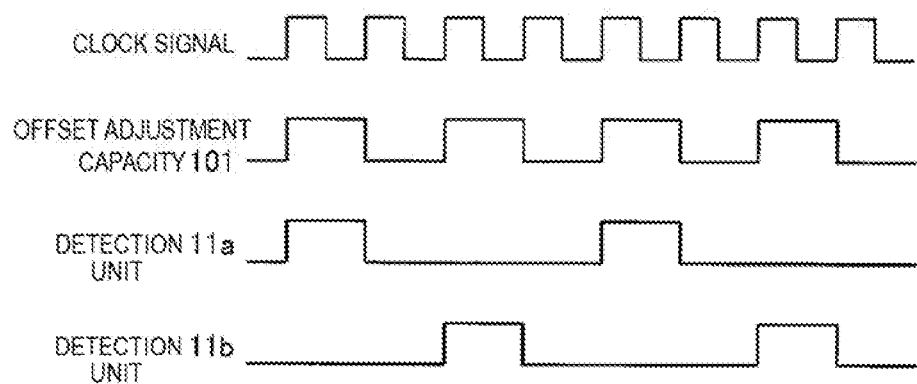
FIG. 4 is a timing chart illustrating an energization operation performed by an energization control circuit of the detection device illustrated in FIG. 3.

Next, the circuit formed as the semiconductor circuit 10 of the detection device 1 will be described with reference to FIGS. 3 and 4. FIG. 3 is a block diagram illustrating a circuit configuration of the detection device 1. FIG. 4 is a timing chart illustrating an energization operation performed by an energization control circuit of the detection device 1.

As illustrated in FIG. 3, the semiconductor circuit 10 includes an offset adjustment capacity 101 (correction capacitive element), an energization control circuit 102, an integrator 103 (difference acquisition circuit), a sample/hold circuit 104, an analog-to-digital (A/D) converter 105 (conversion circuit), and a pulse generator 106. The detection units 11a and 11b are electrically connected to the semiconductor circuit 10 as described above.

The offset adjustment capacity 101 (may also be referred to as an offset adjustment capacitive element) is a capacitive element for correcting the capacitance values (analog values) of the detection units 11a and 11b. The capacitance value (analog value) of the offset adjustment capacity 101 is hereinafter also referred to as a correction capacitance value.

The offset adjustment capacity 101 may be (i) a fixed capacitive element with a fixed correction capacitance value or (ii) a variable capacitive element with a variable correction capacitance value. The offset adjustment capacity 101 may be separately provided outside the semiconductor circuit 10 and may be connected to the semiconductor circuit 10 via a conductive wiring line. The capacitance value of the offset adjustment capacity 101 is set to be close to the capacitance values of the detection units 11a and 11b.

As illustrated in FIG. 4, the energization control circuit 102 controls energization of the detection units 11a and 11b and the offset adjustment capacity 101, in synchronization with the timing of a clock signal generated by the pulse generator 106 described later. Specifically, the energization control circuit 102 controls the energization of the detection units 11a and 11b and the offset adjustment capacity 101 so that one of the detection units 11a and 11b is energized when the offset adjustment capacity 101 is energized and the detection units 11a and 11b are alternately energized. The energization control circuit 102 includes a circuit (not illustrated) that turns ON/OFF the application of power supply voltage to the detection units 11a and 11b and the offset adjustment capacity 101, and performs the energization (application of power supply voltage) with an energization control signal that turns to High level at the timing illustrated in FIG. 4.

The relationship, illustrated in FIG. 4, between the timing of the clock signal and the timing of the energization of the detection units 11a and 11b and the offset adjustment capacity 101 is merely an example. Any timing can be employed as long as the offset adjustment capacity 101 is energized at the timing when one of the detection units 11a and 11b is energized. The energization period is not limited to that illustrated in FIG. 4, and may be longer or shorter than that illustrated in FIG. 4. Furthermore, the order of energization is not necessarily limited to the detection unit 11a and then the detection unit 11b. There may be a down period between the energization periods of the detection units 11a and 11b.

The integrator 103 is a circuit that acquires difference values between capacitance values (also referred to as detected capacitance values) detected by the detection units 11a and 11b and the capacitance value (correction capacitance value) of the offset adjustment capacity 101, and integrates the difference values. The difference acquisition circuit according to one aspect of the present disclosure may have any configuration as long as the difference values can be acquired, and thus the function of integrating the difference values is not necessarily required. Still, the difference values are preferably integrated, for the sake of amplification of the difference values.

The sample/hold circuit 104 is a circuit that samples and holds an integral value output from the integrator 103. Note that the sample/hold circuit 104 can be omitted. The A/D converter 105 is a circuit that converts the analog integral value held by the sample/hold circuit 104 into a digital value.

The pulse generator 106 is a circuit that includes an oscillator and outputs a clock signal of a predetermined cycle. The circuits of the semiconductor circuit 10 (such as the energization control circuit 102, the integrator 103, the sample/hold circuit 104, and the A/D converter 105, for example) operate in synchronization with the clock signal.

The configuration of the semiconductor circuit 10 illustrated in FIG. 3 is merely an example, and thus should not be construed in a limiting sense. For example, the semiconductor circuit 10 may include a register for executing calculation processing, a D/A converter, and an interface for Inter IC Communication (I2C) and Serial Peripheral Interface (SPI) communications and the like, in addition to the circuits illustrated in FIG. 3.

Thus, the semiconductor circuit 10 is not necessarily limited to the configuration illustrated in FIG. 3, and may have any configuration that includes a single offset adjustment capacity 101 and can correct the capacitance values of the two detection units 11a and 11b.

The detection device 1 having the configuration described above operates as described below.

For example, the energization control circuit 102 controls the energization of the detection units 11a and 11b and the offset adjustment capacity 101 at the timing illustrated in FIG. 4. Thus, the capacitance value of one of the detection units 11a and 11b is input to the integrator 103 at the same time as the capacitance value of the offset adjustment capacity 101.

The integrator 103 integrates the difference values described above over a predetermined time period based on the timing of the clock signal, to output the integral value. The sample/hold circuit 104 samples the integral value from the integrator 103 at the timing synchronized with the clock signal, and holds the value while the A/D converter 105 is executing the A/D conversion processing. The A/D converter 105 converts the integral value, output from the sample/hold circuit 104, into a digital signal using the timing synchronized with the clock signal (sampling frequency) and a predetermined number of quantization bits, and sequentially outputs the digital signal as a detection signal (output value) corresponding to the detection units 11a and 11b.

Based on the detection signal thus output, the detection target in contact with the detection units 11a and 11b is detected.

As described above, the detection device 1 according to the present embodiment includes the semiconductor circuit 10, as well as the detection units 11a and 11b, the offset adjustment capacity 101, the integrator 103, and the A/D converter 105 on the semiconductor circuit 10.

Thus, these elements are formed on the semiconductor circuit 10. In particular, with the detection units 11a and 11b formed on the semiconductor circuit 10, the detection device 1 can be configured to have a small size. Furthermore, with the detection units 11a and 11b formed on the semiconductor circuit 10, the influence of a parasitic capacity due to the external wiring line can be reduced. The detection device 1 also has excellent performance in terms of sensitivity as described below. Thus, a small and highly sensitive detection device 1 can be implemented.

The semiconductor circuit 10 of a few millimeter square may be used for the detection device 1 for downsizing. In such a case, the area of each of the detection units 11a and 11b exposed to the detection target (for example, gas) is small. As a result, the change in the capacitance value obtained when the detection target is detected is of a small value relative to the capacitance values of the detection units 11a and 11b. In particular, when the concentration of the detection target is extremely low (when the concentration of the detection target component is in the order of ppm or ppb or lower), the amount of change in the capacitance due to the detection is smaller than the capacitance values of the detection units 11a and 11b by several digits or more.

Thus, a detection signal value (the capacitance change amount) cannot be obtained with a sufficient resolution by performing simple A/D conversion on the capacitance values of the detection units 11a and 11b and outputting the resultant values. For example, when the capacitance values of the detection units 11a and 11b are in the order of pF, in order to detect detection target components in the order of ppm to ppb, the capacitance change amount to be resolved is from the fF order to the aF order.

In view of this, the detection device 1 is configured to correct the capacitance values of the detection units 11a and 11b at the time of detection with the capacitance value of the offset adjustment capacity 101. The offset adjustment capacity 101 is set to be a value close to the capacitance values of the detection units 11a and 11b.

The digital detection signal output from the A/D converter 105 is quantized by the predetermined number of quantization bits of the A/D converter 105. Thus, for a change in capacitance values of the detection units 11a and 11b due to the detection of the detection target, a large number of quantization bits is used to achieve a wide range of capacitance values defined by the number of quantization bits as much as possible (the amount of change (capacity) per bit is set to the smallest possible value).

With this configuration, when a difference between the capacitance value obtained from the detection units 11a and 11b and the capacitance value obtained from the offset adjustment capacity 101 is obtained, high resolution detection of the signal converted by the A/D converter 105 can be achieved with a sufficiently wide range, even if the amount of change in the capacitance values of the detection units 11a and 11b due to the detection of the detection target is small. Thus, high detection sensitivity can be achieved with the comb-shaped electrode 110 with a small area.

The A/D converter 105 employs a circuit with high noise canceling performance (typically, $\Delta\Sigma$ scheme), so that a low noise level can be maintained even when the measurement is performed with a highly sensitive range. The high noise canceling performance given to the A/D converter 105 is advantageous, because generally, the A/D conversion is largely affected by noise.

With a configuration in which two (a plurality of) comb-shaped electrodes 110 are formed on the semiconductor circuit 10 of a few millimeter square, the change in the capacitance obtained by a single comb-shaped electrode 110 could be extremely small depending on the concentration of the detection target. Thus, the detection sensitivity sufficient for such a small change is required. The number of quantization bits of the A/D converter 105 is 12 bits or 18 bits, if the A/D converter 105 is a general purpose product. Still, a larger number of quantization bits of the A/D converter 105 is preferably used to increase the resolution performance. In the present embodiment, a case where the number of quantization bits is 24 bits is described as an example.

The scheme of detecting the change in the capacitance values of the detection units 11a and 11b involves smaller deterioration of the detection material due to thermal noise and energization, than schemes of detecting a change in resistance values.

The detection units 11a and 11b and the comb-shaped electrode 110 form a capacitive element, so that the detection units 11a and 11b can be more easily manufactured than a capacitive element of a parallel plate type with a structure of sandwiching the upper and lower sides of the detection layer 111 with conductive plate members. The capacitive element of a flat plate type requires a complex manufacturing process including forming a lower side electrode, forming the detection layer 111 thereon, and then forming an upper side electrode thereon. On the other hand, the comb-shaped electrode 110 can be formed with a single process. Furthermore, the comb-shaped electrode 110 can achieve a higher detection speed, by setting the area of the detection layer 111 to be in contact with the detection target to be larger than that of the capacitive element of a flat plate type.

Furthermore, correction is performed by switching between the capacitance values output from the plurality of detection units 11a and 11b, so that the capacitance values can be corrected with a single offset adjustment capacity 101. Thus, the number of circuit elements in the semiconductor circuit 10 can be reduced.

Alternatively, each of the detection units 11a and 11b may be provided with the offset adjustment capacity 101. Still, for the sake of downsizing, the capacitance values are preferably corrected with a single offset adjustment capacity 101 provided for the plurality of detection units 11a and 11b.

The capacitance values of the detection units 11a and 11b particularly preferably do not exceed 100 pF. The capacitance value (correction capacitance value) of the offset adjustment capacity 101 is not particularly limited, but is preferably in the fF order or pF order for the correction of the capacitance value of the plurality of detection layers 111. If the offset adjustment capacity 101 is a variable capacity, the correction capacitance value is preferably variable within a predetermined range of approximately 0 to 100 pF.

With the capacitance values of the detection units 11a and 11b and of the offset adjustment capacity 101 set to be within such a range, the minimum detectable (resolvable) capacitance change amount can be in the aF order for the 24-bit A/D converter 105.

If a fixed capacitive element is applied to the offset adjustment capacity 101, the offset adjustment capacity 101 can be easily formed at a low cost. On the other hand, if a variable capacity is applied to the offset adjustment capacity 101, the correction value for the capacitance values of the detection units 11a and 11b can be adjusted in accordance with the capacitance values of the detection units 11a and 11b. Thus, the correction can be highly accurately performed in accordance with the change in the capacitance values of the detection units 11a and 11b, even in a case where the capacitance values of the detection units 11a and 11b change in accordance with the peripheral environment or a long term use. The case where a variable capacity is applied to the offset adjustment capacity 101 will be described in detail in fourth to tenth embodiments described later.

First Modified Example

Figure 5:
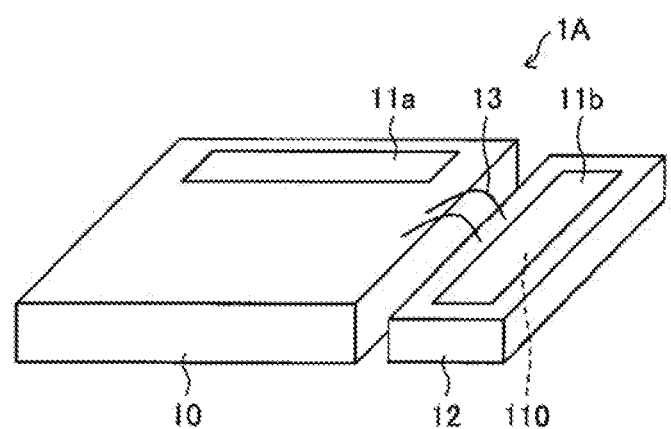
FIG. 5 is a perspective view illustrating a configuration of a detection device according to a modified example of the first embodiment.

A modified example of the present embodiment will be described with reference to FIG. 5. FIG. 5 is a perspective view illustrating a configuration of a detection device 1A according to the present modified example.

As illustrated in FIG. 5, the detection device 1A includes the detection unit 11a formed on the semiconductor circuit 10 and the detection unit 11b formed on a substrate 12 provided separately from the semiconductor circuit 10. The comb-shaped electrode 110 formed on the detection unit 11b is connected to the semiconductor circuit 10 via a conductive wiring line 13. Specifically, the detection unit 11b is connected to the semiconductor circuit 10 via the conductive wiring line 13.

As described above, in the detection device 1A according to the present modified example, not all the plurality of detection units needs to be formed on the semiconductor circuit 10. Some of the detection units (the detection unit 11b, for example) may be formed outside the semiconductor circuit 10 and may be electrically connected to the semiconductor circuit 10. With this configuration, the detection unit 11b is disposed sufficiently close to the semiconductor circuit 10 so that the conductive wiring line 13 can be provided by wire bonding, and thus the influence of the parasitic capacity can be reduced.

The configuration where the detection unit 11b is formed on the substrate 12 is advantageous also in terms of manufacturing. The configuration where the detection units 11a and 11b are formed on the semiconductor circuit 10 requires films of different materials to be coated or formed on the comb-shaped electrode 110 for forming the detection layers 111 each of the detection units 11a and 11b. For example, when the detection device 1 illustrated in FIG. 1 is prepared using a wafer and the detection units 11a and 11b are formed on the semiconductor circuit 10, the detection layers 111 need to be formed using different materials for the detection units 11a and 11b on the wafer.

On the other hand, when the detection unit 11a is formed on the semiconductor circuit 10 and the detection unit 11b is formed on the substrate 12, wafers corresponding to the materials of the detection layers 111 are prepared in advance, and the semiconductor circuit 10 and the substrate 12 are cut out from the respective wafers, to be assembled into the detection device 1A. Thus, manufacturing free of the cumbersomeness of the coating or film forming can be achieved.

Second Modified Example

Another modified example of the present embodiment will be described.

Here, the offset adjustment capacity 101 for the detection units 11a and 11b on a single semiconductor circuit 10 is a fixed capacitive element. In this configuration, variation of the properties (the dielectric constant and the polarizability, in particular) of different materials used for the detection layers 111 of the detection units 11a and 11b needs to be taken into consideration for equalizing the capacitance values between the detection units 11a and 11b. Thus, in the present modified example, the film thicknesses (thicknesses) of the detection layers 111 used for the detection units 11a and 11b are adjusted to achieve capacitance values of the detection units 11a and 11b that are close to each other.

The detection units 11a and 11b are different from each other in the type of the material of the detection layers 111. Under such a basic condition, the capacitance values of the detection units 11a and 11b can be substantially equalized by changing the thickness of the layer depending on the material used.

For example, the detection layer 111 using a material with a high dielectric constant is formed to be thin, and the detection layer 111 using a material with a low dielectric constant is formed to be thick. In the comb-shaped electrode 110, the dielectric constant of a dielectric member can be sensed as a capacitor within a range where an electric line of force is produced, and thus the thickness of the detection layer 111 is changed within such a range.

Thus, the capacitance values of the detection units 11a and 11b are set to be close to each other with an adjustment of reducing the thicknesses if the capacitance values are excessively large, and of increasing the thicknesses if the capacitance values are excessively small. With the detection units 11a and 11b thus having the detection layers 111 with different materials and thicknesses, the capacitance values of the detection units 11a and 11b are set to be close to each other.

The detection layers 111 formed of different materials as described above may be formed to have thicknesses to achieve the capacitance values of the detection units 11a and 11b within a predetermined range. With this configuration, even if a single fixed capacitive element is used for the offset adjustment capacity 101, the correction value for the capacitance values of the detection units 11a and 11b can be set to be closer to 0, compared with a case where the detection units 11a and 11b have the detection layers 111 with the same thickness. Thus, the detection range for the corrected capacitance values can be increased, whereby A/D conversion of the corrected capacitance values can be performed with high resolution.

Now, a case is described where a 24-bit A/D converter is used as the A/D converter 105 for measuring the capacitance values of the detection units 11a and 11b in an atmosphere (specifically, in the air or a nitrogen atmosphere) with no gas serving as the detection target. In such a case, assuming that the minimum capacitance value that can be practically resolved by the A/D converter 105 is 1 aF, the upper limit (full scale) of the measurable capacitance is 16.78 pF (=1 aF×$2^{24}$). Thus, with the capacitance values of the detection units 11a and 11b set to be close to each other with the difference therebetween being roughly equal to or smaller than 10 pF (predetermined value), a slight change in the capacitance value due to exposure to a low concentration detection target can be detected with high detection sensitivity ensured for all of the detection units 11a and 11d, even if the value of the offset adjustment capacity 101 is fixed.

With the capacitance values of a plurality of detection units corrected with a single offset adjustment capacity 101, highly sensitive measurement can be achieved even when the offset adjustment capacity 101 is a fixed capacitive element.

Second Embodiment

Hereinafter, a second embodiment of the present disclosure will be described with reference to FIG. 6 to FIG. 8. Note that, for convenience of explanation, components illustrated in respective embodiments are designated by the same reference numerals as those having the same function, and the descriptions of these components will be omitted. The same applies to embodiments after the present embodiment.

Figure 6:
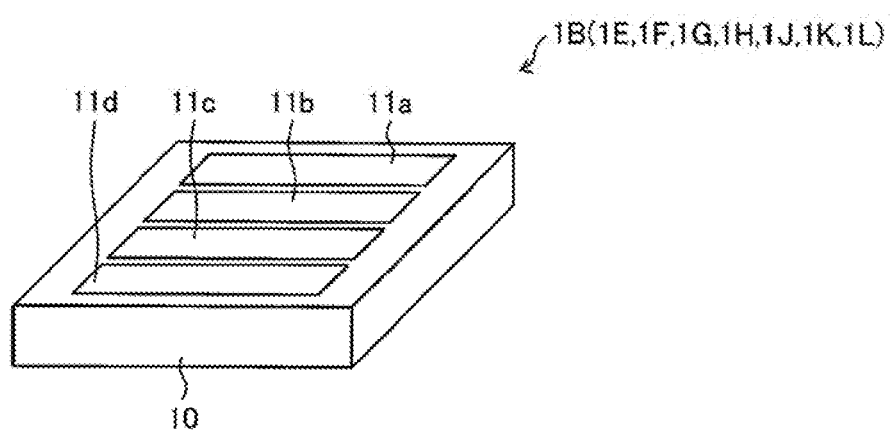
FIG. 6 is a perspective view illustrating a configuration of an outer appearance of a detection device according to second and fourth to tenth embodiments of the present disclosure.

FIG. 6 is a perspective view illustrating a configuration of an outer appearance of a detection device 1B according to the second embodiment. FIG. 7 is a block diagram illustrating a circuit configuration of the detection device 1B. FIG. 8 is a timing chart illustrating an energization operation performed by an energization control circuit of the detection device 1B.

The detection device 1 includes the two detection units 11a and 11b in the first embodiment described above, but may also include three or more detection units. In the present embodiment, the detection device 1B including four detection units 11a to 11d as illustrated in FIG. 6 is described as an example of such a configuration.

The detection device 1B includes the semiconductor circuit 10, and the four detection units 11a to 11d are formed on the semiconductor circuit 10 to be arranged side by side. The detection units 11c and 11d have configurations that are similar to those of the detection units 11a and 11d described above in the first embodiment, and thus the detailed description thereof will be omitted herein.

When detection targets of the detection units 11a to 11d are different types of gases, the detection layers 111 (not illustrated in FIG. 6) of the detection units 11a to 11d are made of different materials so that the detection units 11a to 11d provide different responses, that is, patterns different from each other in the amount of change in the capacitance values.

Figure 7:
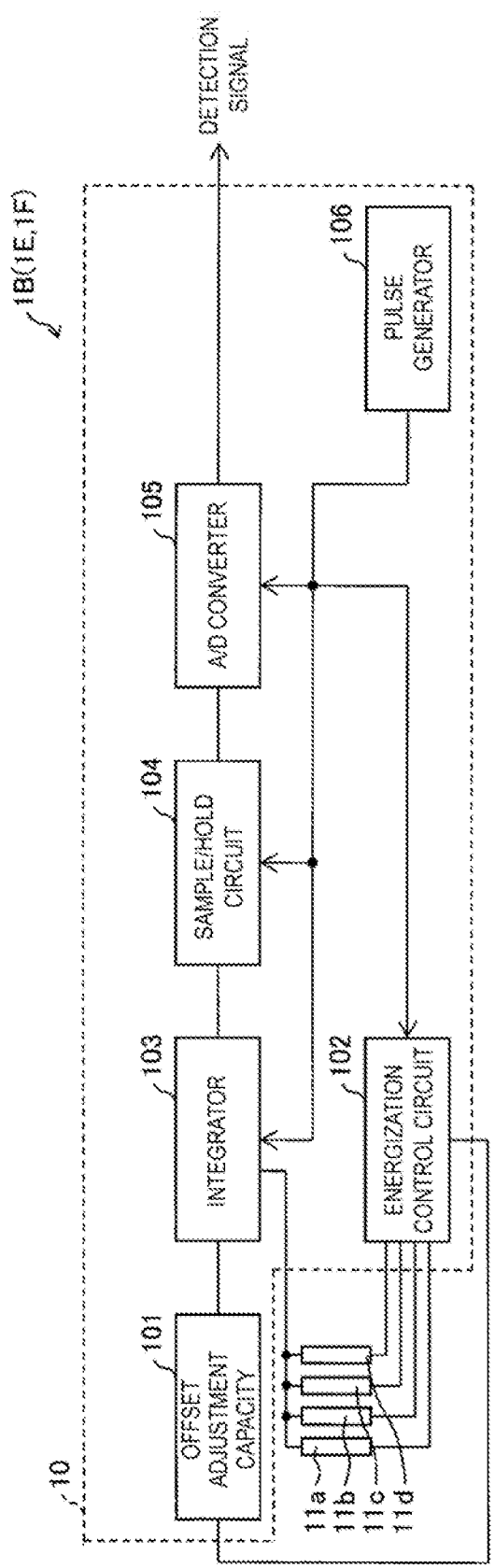
FIG. 7 is a block diagram illustrating a circuit configuration of the detection device illustrated in FIG. 6.

The semiconductor circuit 10 according to the present embodiment illustrated in FIG. 7 has the same configuration as the semiconductor circuit 10 of the detection device 1 except for the number of detection units. Also in the present embodiment, the detection units 11a to 11d are electrically connected to the semiconductor circuit 10.

The energization control circuit 102 controls the energization of the offset adjustment capacity 101 and of the detection units 11a and 11b in the detection device 1, and controls the energization of the offset adjustment capacity 101 and of the detection units 11a to 11d in the detection device 1B.

Figure 8:
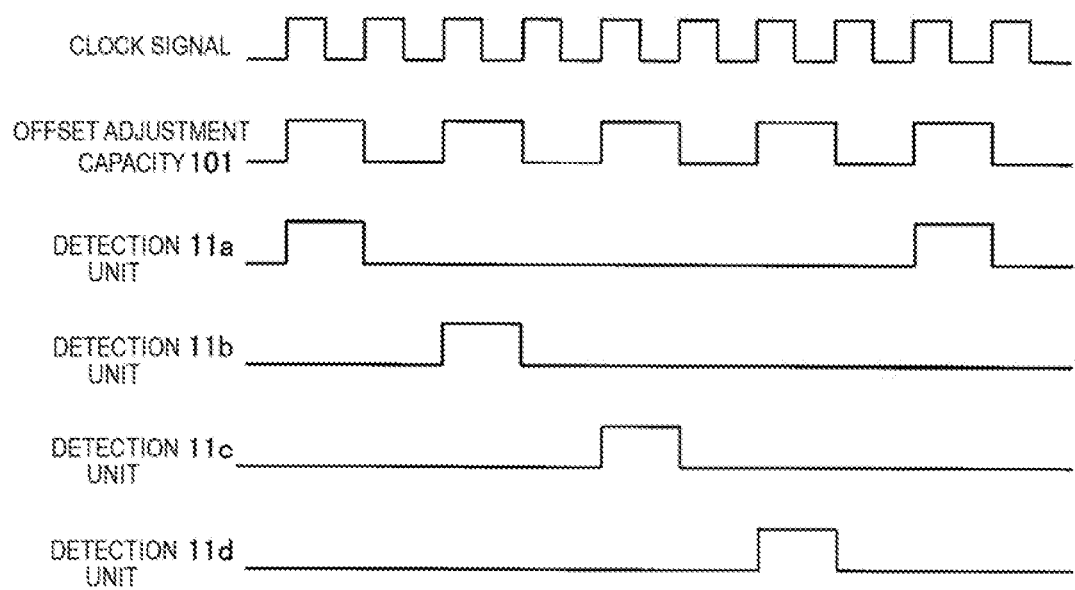
FIG. 8 is a timing chart illustrating an energization operation performed by an energization control circuit of the detection device illustrated in FIG. 7.

Specifically, as illustrated in FIG. 8, the energization control circuit 102 controls the energization of the detection units 11a to 11d and the offset adjustment capacity 101 so that one of the detection units 11a to 11d is energized when the offset adjustment capacity 101 is energized and the detection units 11a to 11d are sequentially energized.

The relationship, illustrated in FIG. 8, between the timing of the clock signal and the timing of the energization to the detection units 11a to 11d and the offset adjustment capacity 101 is merely an example. Any timing can be employed as long as the offset adjustment capacity 101 is energized at the timing when one of the detection units 11a to 11d is energized. The energization period is not limited to that illustrated in FIG. 8, and may be longer or shorter than that illustrated in FIG. 8. Furthermore, the order of energization is not necessarily limited to being from the detection unit 11a to the detection unit 11d. There may be a down period between the energization periods of the detection units 11a to 11d.

In the detection device 1B, for example, the energization control circuit 102 controls the energization of the detection units 11a to 11d and the offset adjustment capacity 101 at the timing illustrated in FIG. 8. Thus, the capacitance value of one of the detection units 11a to 11d is input to the integrator 103 at the same time as the capacitance value of the offset adjustment capacity 101. The detection target in contact with the detection units 11a to 11d is detected based on the detection signal output from the A/D converter 105 through processing that is the same as that in the first embodiment.

As described above, the detection device 1B according to the present embodiment includes the semiconductor circuit 10, as well as the detection units 11a to 11d formed on the semiconductor circuit 10. Thus, the detection device 1B can be configured to have a small size. Furthermore, with the detection units 11a to 11d formed on the semiconductor circuit 10, the influence of a parasitic capacity due to the external wiring line can be reduced.

In addition, the detection device 1B is configured to correct the capacitance values of the detection units 11a to 11d at the time of detection with the capacitance value of the offset adjustment capacity 101. The offset adjustment capacity 101 is set to be a value close to the capacitance values of the detection units 11a to 11d.

With this configuration, when a difference between the capacitance value obtained from the detection units 11a to 11d and the capacitance value obtained from the offset adjustment capacity 101 is obtained, high resolution detection of the signal converted by the A/D converter 105 can be achieved with a sufficiently expanded range, even if the amount of change in the capacitance values of the detection units 11a to 11d due to the detection of the detection target is small. Thus, high detection sensitivity can be achieved with the comb-shaped electrode 110 with a small area.

The offset adjustment capacity 101 may be a fixed capacitive element or variable capacitive element, may be separately provided outside the semiconductor circuit 10, and may be connected to the semiconductor circuit 10 via a conductive wiring line.

The detection device 1B has three or more detection units, so that known multivariate analyses such as main component analysis, independent component analysis, and cluster analysis and the like can be applied to identify a wide variety of detection targets. The type of gas that can be detected as the detection target with a single detection unit depends on the material of the detection layer 111. Specifically, if a material with strong selectivity relative to the detection target is used, only a certain detection target can be detected. If a material enabling various detection targets to be detected is used, a plurality of detection targets can be detected. Thus, with three or more detection units of different types prepared, detection targets can be identified through predetermined equations based on detection values of the detection units.

Detection of gas is likely to be affected by humidity in the atmosphere. In view of this, the detection unit 11a is provided as a first detection unit (humidity sensor) that is highly reactive to water vapor, and the detection units 11b to 11d are provided as second detection units that are less reactive to water vapor than the detection unit 11a and react with other types of gases. The influence of the humidity that somewhat affects the second detection units is canceled (humidity correction) based on the detection value from the first detection unit. With the first detection unit provided as the humidity sensor, the humidity correction can be performed for the humidity changing depending on the environment.

Modified Example

A modified example of the present embodiment will be described.

In the present modified example, the second modified example of the first embodiment is applied, and the film thicknesses of the detection layers 111 of the detection units 11a to 11d are adjusted to achieve capacitance values of the detection units 11a to 11d that are close to each other. Details of the adjustment are the same as in the second modified example of the first embodiment, and the detailed description thereof will be omitted herein.

In this manner, the thicknesses of the detection layers 111 of the detection units 11a to 11d are set. With this configuration, even if a single fixed capacitive element is used for the offset adjustment capacity 101, the correction value for the capacitance values of the detection units 11a to 11d can be set to be closer to 0, compared with a case where the detection units 11a to 11d have the detection layers 111 with the same thickness. Thus, the detection range for the corrected capacitance values can be increased, whereby A/D conversion of the corrected capacitance values can be performed with high resolution.

Third Embodiment

Figure 9:
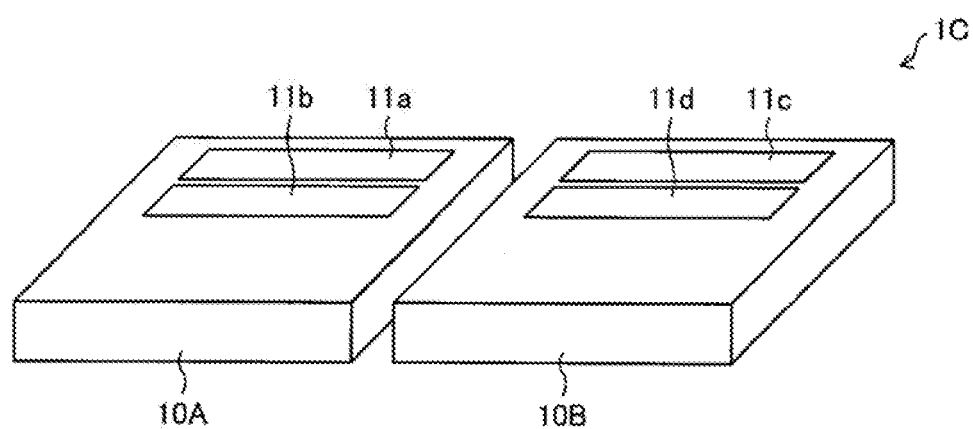
FIG. 9 is a perspective view illustrating a configuration of an outer appearance of a detection device according to a third embodiment of the present disclosure.
Figure 10:
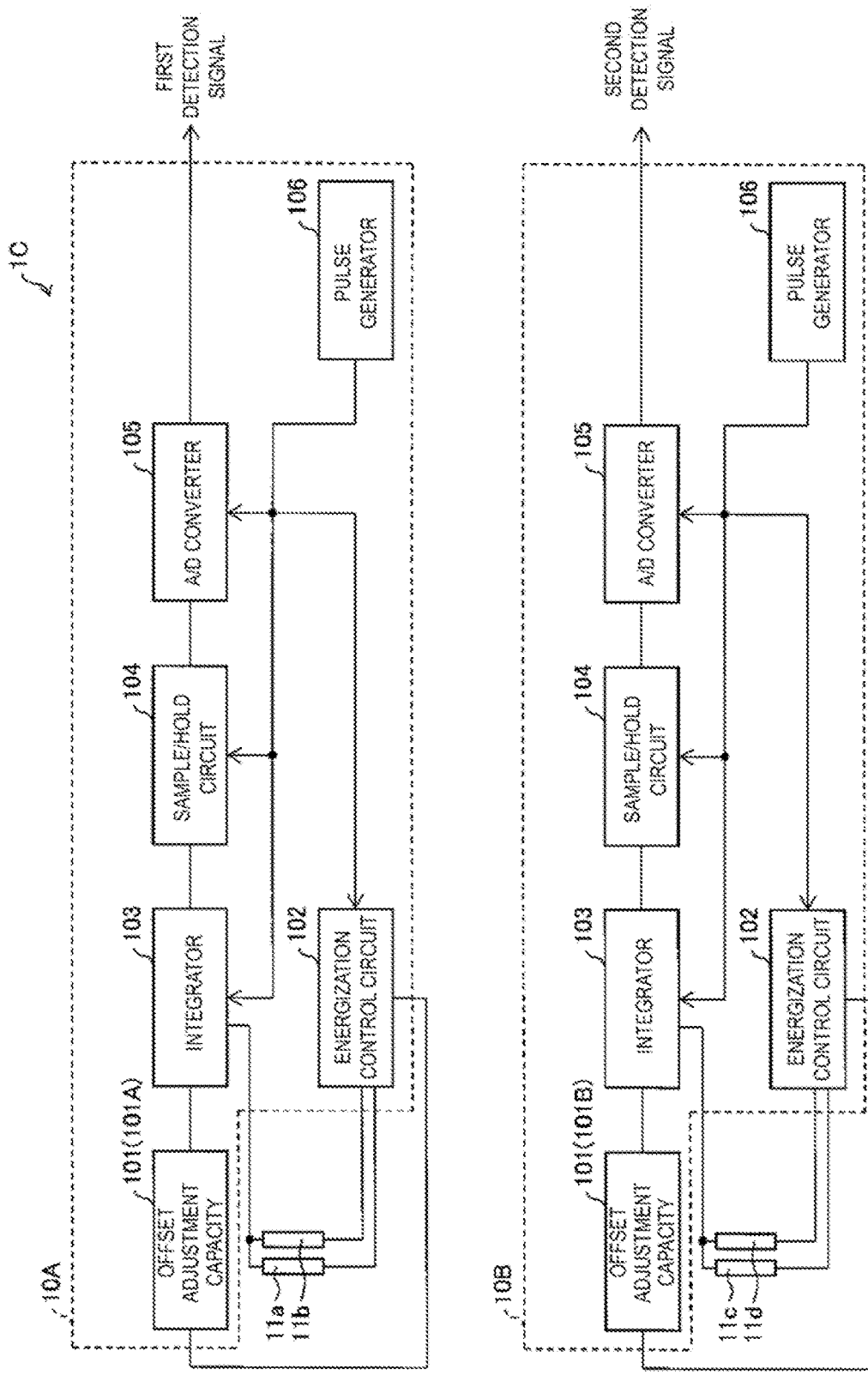
FIG. 10 is a block diagram illustrating a circuit configuration of the detection device illustrated in FIG. 9.

Hereinafter, a third embodiment of the present disclosure will be described with reference to FIG. 9 and FIG. 10. FIG. 9 is a perspective view illustrating a configuration of an outer appearance of a detection device 1C according to the third embodiment. FIG. 10 is a block diagram illustrating a circuit configuration of the detection device 1C.

As illustrated in FIG. 9, the detection device 1C includes two semiconductor circuits 10A and 10B. The two detection units 11a and 11b are formed on the semiconductor circuit 10A, and the two detection units 11c and 11d are formed on the semiconductor circuit 10B. Similar materials are used for the detection layers 111 of the detection units 11a and 11b. Similar materials are used for the detection layers 111 of the detection units 11c and 11d.

As illustrated in FIG. 10, the semiconductor circuits 10A and 10B each have members similar to those of the semiconductor circuit 10 described above (see FIG. 3). In the present embodiment, offset adjustment capacities 101 may be distinguished from each other with the offset adjustment capacity 101 provided to the semiconductor circuit 10A also referred to as an offset adjustment capacity 101A, and the offset adjustment capacity 101 provided to the semiconductor circuit 10B also referred to as an offset adjustment capacity 101B.

The detection units 11a and 11b are electrically connected to the semiconductor circuit 10A, and the detection units 11c and 11d are electrically connected to the semiconductor circuit 10B. In the semiconductor circuit 10A, like in the semiconductor circuit 10, the energization of the detection units 11a and 11b and of the offset adjustment capacity 101A is controlled, so that a first detection signal is output. In the semiconductor circuit 10B, like in the semiconductor circuit 10, the energization of the detection units 11c and 11d and of the offset adjustment capacity 101B is controlled, so that a second detection signal is output.

The first detection signal and the second detection signal can each be used for determining a detection target. Some detection targets may be determined based on the first detection signal and the second detection signal, by the semiconductor circuits 10A and 10B, or an external control circuit separately provided.

As described above, the detection device 1C includes the individual semiconductor circuits 10A and 10B each provided with the offset adjustment capacities 101 (offset adjustment capacities 101A, 101B). With this configuration, a single offset adjustment capacity 101 can correct the capacitance values of the semiconductor circuits 10A and 10B with the detection layers 111 made of materials with similar temperature/humidity characteristics and drift characteristics.

Thus, if the offset adjustment capacity 101 (offset adjustment capacities 101A, 101B) is a fixed capacitive element, even when drift due to a change in the characteristics of the material of the detection layer 111 occurs, a highly sensitive detection state can be maintained for the detection units 11a and 11b in the semiconductor circuit 10A and the detection units 11c and 11d in the semiconductor circuit 10B without reducing the detection range.

It would not be necessarily easy to substantially equalize the capacitance values of multiple (four or more, for example) detection units on a single semiconductor circuit.

Still, the capacitance values of two similar detection units are relatively easy to equalize. Thus, the two similar detection units 11b and 11b and the two similar detection units 11c and 11d are respectively provided on the different semiconductor circuits 10A and 10B, so that the offset adjustment capacity of the fixed capacitive element can be easily corrected.

If the capacitance value cannot be appropriately corrected by the offset adjustment capacity 101, the upper limit (full scale) of the measurable capacitance needs to be set to achieve a wide range for the A/D converter 105. This results in an inevitable increase in the amount of change in the capacitance value per bit, rendering the resolution increase impossible. To avoid such a disadvantage, the corrected capacitance value is preferably set to be close to 0 as much as possible.

As described above, two similar detection units involve a small difference in drift due to a change in the characteristics of the material of the detection layer 111, and thus the capacitance values thereof are less likely to vary. Thus, the corrected capacitance value can be set to be close to 0 as much as possible.

Not all the plurality of semiconductor circuits may be provided with a plurality of detection units, and a part of the plurality of semiconductor circuits may be provided with a single detection unit.

Three or more detection units (for example, the four detection units 11a to 11d as illustrated in FIG. 6) may be formed on each of the semiconductor circuits 10A and 10B. Alternatively, two detection units may be formed on one of the semiconductor circuits 10A and 10B and three or more detection units may be formed on the other one of the semiconductor circuits 10A and 10B. The capacitance values of the three or more detection units are corrected with a single offset adjustment capacity 101, as in the case of the detection device 1C according to the second embodiment.

Modified Example

Figure 11:
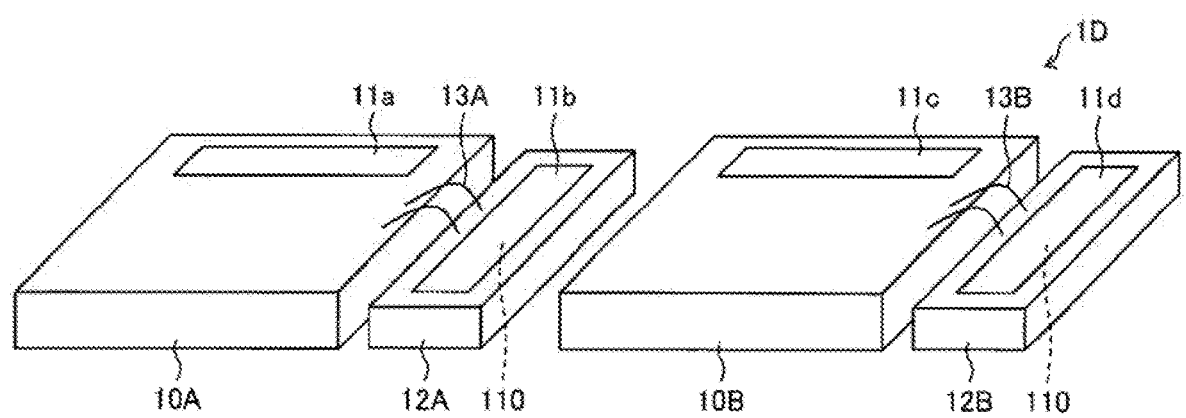
FIG. 11 is a perspective view illustrating a configuration of a detection device according to a modified example of the third embodiment.

A modified example of the present embodiment will be described with reference to FIG. 11. FIG. 11 is a perspective view illustrating a configuration of a detection device 1D according to the present modified example. As illustrated in FIG. 11, the detection device 1D includes substrates 12A and 12B, as well as the semiconductor circuits 10A and 10B.

The detection unit 11a is formed on the semiconductor circuit 10A, and the detection unit 11b is formed on the substrate 12A provided separately from the semiconductor circuit 10A. The comb-shaped electrode 110 formed on the detection unit 11b is connected to the semiconductor circuit 10A via a conductive wiring line 13A.

The detection unit 11c is formed on the semiconductor circuit 10B, and the detection unit 11b is formed on the substrate 12B provided separately from the semiconductor circuit 10B. The comb-shaped electrode 110 formed on the detection unit 11d is connected to the semiconductor circuit 10B via a conductive wiring line 13B.

As described above, in the detection device 1D, some of the detection units (the detection units 11b and 11d) may be formed outside the semiconductor circuits 10A and 10B and may be electrically connected to the semiconductor circuits 10A and 10B. With this configuration, the detection units 11b, 10d are disposed sufficiently close to the semiconductor circuits 10A and 10B so that the conductive wiring line 13A and the conductive wiring line 13B can be provided by wire bonding, and thus the influence of the parasitic capacity can be reduced.

With the detection units 11b and 11c formed on the substrates 12A and 12B, as in the modification example (the detection device 1A) of the first embodiment, the formation of the detection layer 111 free of the cumbersomeness of the coating or film forming of material can be achieved, which is advantageous in manufacturing.

Fourth Embodiment

Hereinafter, a fourth embodiment of the present disclosure will be described with reference to FIG. 6, FIG. 12, and FIGS. 13A and 13B. As illustrated in FIG. 6, a detection device 1E according to the present embodiment has an outer appearance similar to that of the detection device 1B according to the second embodiment.

Figure 12:
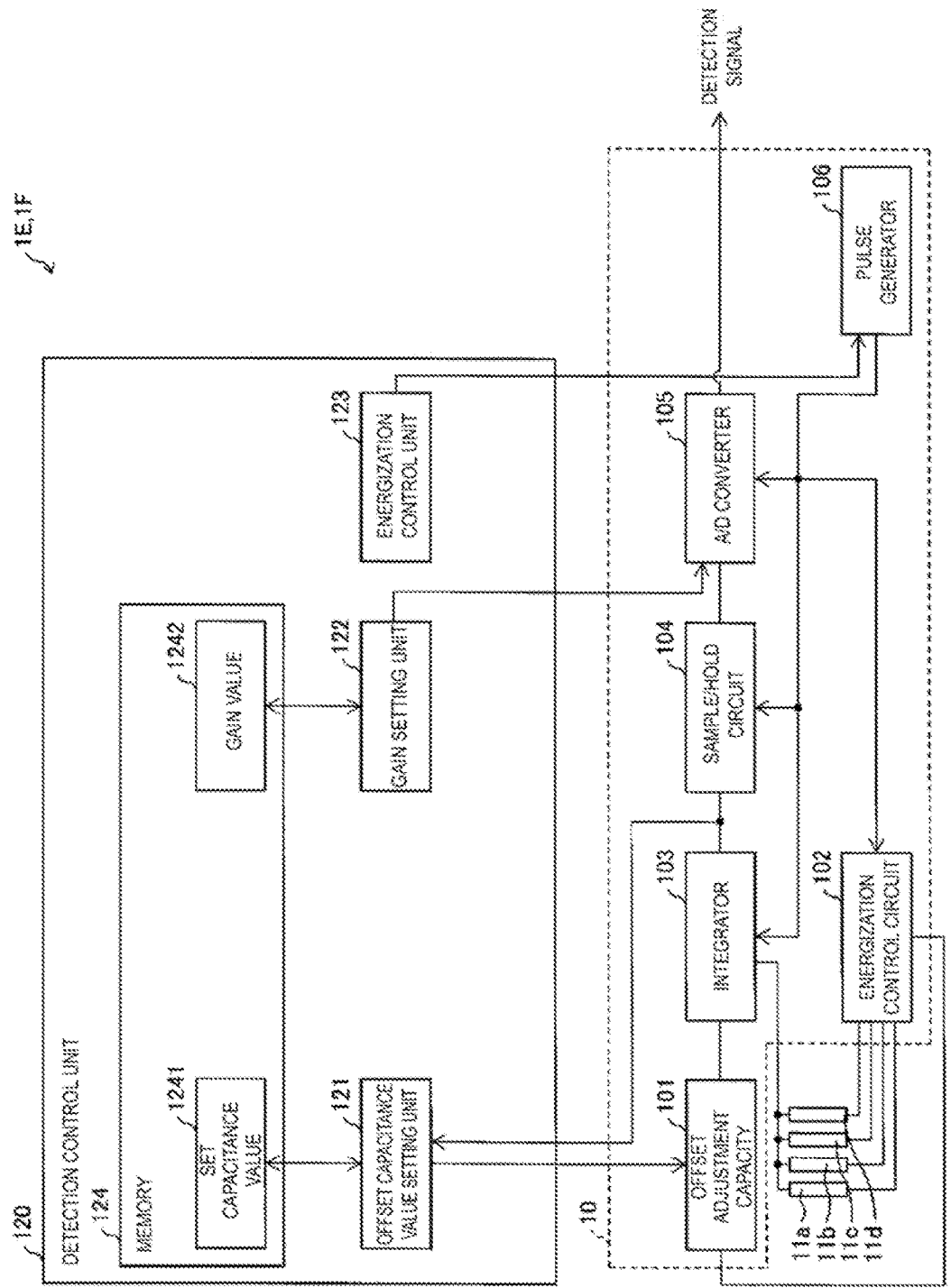
FIG. 12 is a block diagram illustrating a system configuration of the detection device according to the fourth and fifth embodiments of the present disclosure.

FIG. 12 is a block diagram illustrating a system configuration of the detection device 1E. As illustrated in FIG. 12, like the detection device 1B, the detection device 1E includes a single offset adjustment capacity 101 for four detection units 11a to 11d on the semiconductor circuit 10. The detection device 1E includes the members of the detection device 1B and further includes a detection control unit 120.

In the present embodiment, the offset adjustment capacity 101 is a variable capacitive element. The capacitance value (correction capacitance value) of this variable capacitive element is adjusted by the detection control unit 120 described below. For example, the offset adjustment capacity 101 is an element using a variable capacity diode to have the capacity changed by applied voltage, or includes a plurality of capacity cells and transistor circuits provided to the respective capacity cells. The transistor circuits are connected in parallel with the other capacity cells upon being turned ON, and are disconnected from the other capacity cells upon being turned OFF. The offset adjustment capacity 101 has a capacitance value varying depending on a combination of capacity cells to be connected to each other in parallel. The offset adjustment capacity 101 (variable capacitive element) having such a configuration is merely an example, and should not be construed in a limiting sense.

The detection control unit 120 includes an offset capacitance value setting unit 121 (capacitance value setting unit), a gain setting unit 122, an energization control unit 123, and a memory 124. The detection control unit 120 may be formed in the semiconductor circuit 10 or may include a microcomputer or the like provided outside the semiconductor circuit 10.

The offset capacitance value setting unit 121 sets a capacitance value of the offset adjustment capacity 101 (hereinafter, referred to as an offset capacitance value). As described below, the offset capacitance value setting unit 121 adjusts and sets the offset capacitance value in accordance with the capacitance value corrected by the integrator 103 (the difference value of the capacitance values obtained by the integrator 103).

Specifically, the offset capacitance value setting unit 121 adjusts the capacitance value of the offset adjustment capacity 101 to be within a predetermined range, and sets the capacitance value adjusted to be within the predetermined range as an offset capacitance value. The offset capacitance value setting unit 121 stores the offset capacitance value thus set in the memory 124 as an adjusted capacitance value (also referred to as a set capacitance value). A set capacitance value 1241 illustrated in FIG. 12 represents the adjustment capacitance value (set capacitance value) stored in the memory 124.

When a detection operation (a detection mode described later) is performed, the offset capacitance value setting unit 121 reads the adjustment capacitance value from the memory 124, and when each of the detection units 11a to 11d is energized, the offset capacitance value setting unit 121 changes the offset capacitance value to be the adjustment capacitance value corresponding to the detection units 11a to 11d. The adjustment capacitance value is adjusted with the applied voltage when a variable capacity diode is employed. When a plurality of capacity cells are employed, the adjustment capacitance value is provided as binary data indicating a connected state (1) or a disconnected state (0) of each of the capacity cells.

The gain setting unit 122 sets a gain value determined in advance. The gain value is an index indicating a range of detectable capacitance values. Specifically, the gain setting unit 122 designates the range of capacitance values allocated to the number of quantization bits of the A/D converter 105, to the A/D converter 105.

The energization control unit 123 starts the pulse generator 106 so that the energization control circuit 102 operates, when a power source device (not illustrated) provided outside the detection device 1E is turned ON (when the power is turned ON). The gain value set in advance is stored in the memory 124 as a gain value 1242.

Figure 13A:
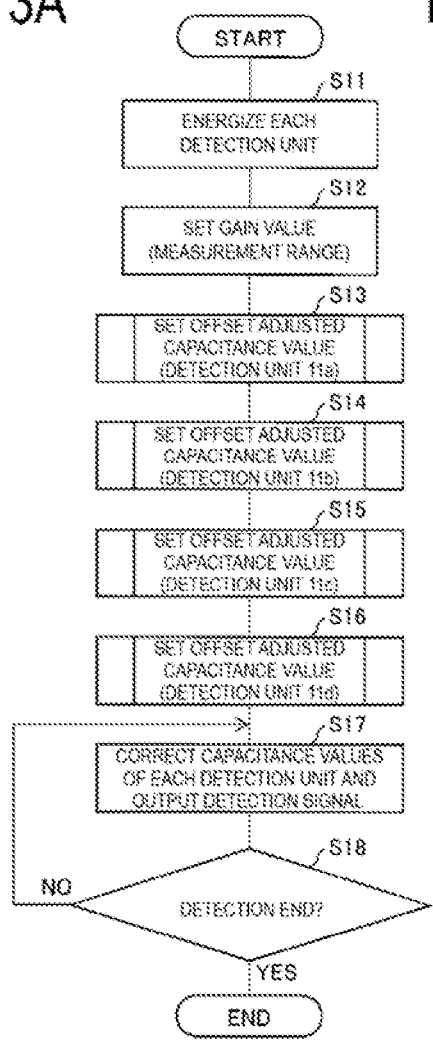
FIG. 13A is a flowchart illustrating a procedure for detecting a detection target performed by the detection device according to the fourth embodiment of the present disclosure.
Figure 13B:
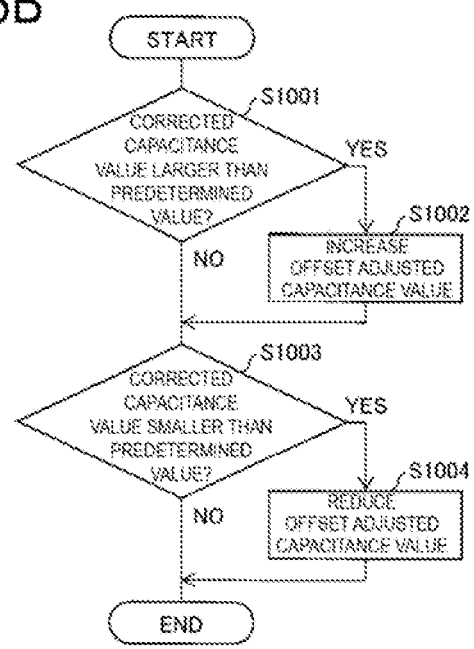
FIG. 13B is a flowchart illustrating a part of the procedure illustrated in FIG. 13A in detail.

A detection operation performed by the detection device 1E having the configuration described above will be described. FIG. 13A is a flowchart illustrating a procedure (control method) for detecting a detection target performed by the detection device 1E according to the fourth embodiment. FIG. 13B is a flowchart illustrating a part of the procedure illustrated in FIG. 13A in detail.

The detection device 1E operates under two modes including a setting mode of executing setting processing at the time of start-up and a detection mode to be achieved after the setting processing is completed. As illustrated in FIG. 13A, first of all, the energization control unit 123 operates the energization control circuit 102 to energize the detection units 11a to 11d (step S11). In this energized state, the setting mode starts, and the gain setting unit 122 reads the gain value from the memory 124 and sets the gain value to the A/D converter 105 (step S12).

The gain value may be a value determined in advance based on the change amount at the time of detection of the detection target and a change in the capacitance values of the detection units 11a to 11d due to a change in the expected use environment of the detection device 1E. The gain value may be set as described above, and then may be changed at the time of detection.

In changing the gain, increasing the gain value corresponds to narrowing the range of detectable capacitance values with the number of quantization bits of the A/D converter 105, that is, raising the resolution. In changing the gain, decreasing the gain value corresponds to widening the range of detectable capacitance values with the number of quantization bits of the A/D converter 105, that is, lowering the resolution. The gain value is set to be a gain value expected in advance for mass production (manufacturing) of the detection device 1E, but may be a value corresponding to the resolution settable by the user.

Then, the offset capacitance value setting unit 121 sets the offset capacitance value corresponding to the detection unit 11a (step S13). Next, the offset capacitance value setting unit 121 sets the offset capacitance value corresponding to the detection unit 11b (step S14). Subsequently, the offset capacitance value setting unit 121 sets the offset capacitance value corresponding to the detection unit 11c (step S15). Furthermore, the offset capacitance value setting unit 121 sets the offset capacitance value corresponding to the detection unit 11d (step S16).

Steps S13 to S16 may be collectively referred to as a capacitance value setting process. The processing in steps S13 to S16 (capacitance value setting process) will be described in detail with reference to FIG. 13B described later. After step S16, the offset capacitance value setting unit 121 writes the capacitance values set for the respective detection units 11a to 11d, as adjustment capacitance values, to the memory 124.

When the offset capacitance values are set as described above, the setting mode is completed, and the detection device 1E transitions to the detection mode. In the detection mode, the integrator 103 corrects the capacitance values of the detection units 11a to 11d with the capacitance value of the offset adjustment capacity 101, and then, the A/D converter 105 converts the corrected capacitance value to a digital signal and outputs a detection signal as described above in the first embodiment (step 17). The detection control unit 120 repeatedly executes the processing in step S17 until the detection processing is completed (step S18).

In the processing in step S17, as the energization control circuit 102 switches the energization target one by one among the detection units 11a to 11d, the offset capacitance value setting unit 121 reads the adjustment capacitance values set to the selected one of the detection units 11a to 11d from the memory 124, and switches the offset capacitance value into the adjustment capacitance value.

Next, a procedure of setting the offset capacitance value corresponding to each of the detection units 11a to 11d in steps S13 to S16 (capacitance value setting process) will be described with reference to FIG. 13B.

First of all, the offset capacitance value setting unit 121 determines whether the capacitance value corrected by the integrator 103 is larger than a predetermined upper limit value (step S1001). Upon determining that the corrected capacitance value (output value from the integrator 103) is larger than the upper limit value (YES), the offset capacitance value setting unit 121 increases the offset capacitance value (adjustment capacitance value) by a predetermined value (step S1002), and continuously executes the processing in step S1001 until the corrected capacitance value is determined to be equal to or smaller than the upper limit value (NO).

Upon determining that the corrected capacitance value is equal to or smaller than the upper limit value (NO), the offset capacitance value setting unit 121 determines whether the corrected capacitance value is smaller than a predetermined lower limit value (step S1003). Upon determining that the corrected capacitance value is smaller than the lower limit value (YES), the offset capacitance value setting unit 121 decreases the adjustment capacitance value by a predetermined value (step S1004), and continuously executes the processing in step S1003 until the corrected capacitance value is determined to be equal to or larger than the lower limit value (NO).

As described above, in the capacitance value setting process, the offset capacitance value setting unit 121 adjusts the offset capacitance value to be a value within a predetermined range (equal to or smaller than the upper limit value and equal to or larger than the lower limit value) to set the offset capacitance value.

Generally, it is not easy to set the value of the offset adjustment capacity to set the corrected capacitance value to be a value sufficiently close to 0. Thus, in the present embodiment, the value of the offset adjustment capacity is set so that the corrected capacitance value falls within the predetermined range as described above.

The predetermined range may be determined to be within a detection range, that is, not to overwhelm the number of quantization bits of the A/D converter 105, and may be set to be narrower within such a range.

The detection signal (measurement value) acquired and output in step S17 may be a sum of results obtained over a time period or a predetermined number of times, or may be a result of executing filtering processing. A standby period may be provided in a series of processing in steps S11 to S18.

As described above, in the detection device 1E according to the present embodiment, the detection control unit 120 adjusts the offset capacitance value in accordance with the difference value obtained by the integrator 103. Thus, the detection device 1E includes the detection control unit 120 to be capable of setting the offset capacitance value to each of the detection units 11a to 11d, and of correcting the capacitance values of each of the detection units 11a to 11d using the capacitance value thus set.

To keep the offset capacitance value unchanged as much as possible, the capacitance values of the plurality of detection units 11a to 11d are preferably set to be at values that are equal to each other as much as possible, at the time when the units 11a to 11d (the comb-shaped electrode 110) are formed. However, it is not necessarily easy to highly precisely equalize the capacitance values of the detection units 11a to 11d. Thus, the present embodiment employs a realistic method of adjusting the offset capacitance value for the capacitance value of each of the detection units 11a to 11d.

With this method, the capacitance value of the offset adjustment capacity 101 can be adjusted to be close to the capacitance value of each of the detection units 11a to 11d, even when where is no reference information for setting the offset capacitance value. Thus, the capacitance values of the detection units 11a to 11d can be highly accurately corrected. Thus, even when the concentration of the detection target (gas) is extremely low, a minute change in the capacitance value due to the detection can be detected with high resolution.

Before the detection device 1E performs the detection, the offset capacitance value is individually set even when the capacitance values of the detection units 11a to 11d drift under an influence of an environment and the like due to a long term use, for example. Thus, the influence of the drift can be canceled (canceled out).

In the present embodiment, the detection device 1E includes the four detection units 11a to 11d, but is not limited to this configuration, and may include two or more detection units. The same applies to embodiments described below.

Fifth Embodiment

Figure 14:
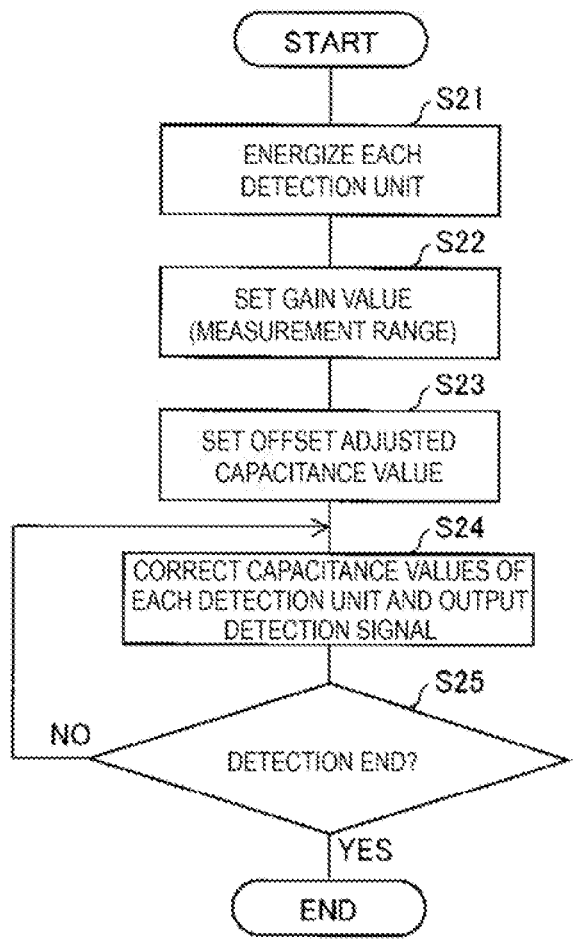
FIG. 14 is a flowchart illustrating a procedure for detecting a detection target performed by the detection device according to the fifth embodiment of the present disclosure.

Hereinafter, a fifth embodiment of the present disclosure will be described with reference to FIG. 6, FIG. 12, and FIG. 14. As illustrated in FIG. 6 and FIG. 12 described above, a detection device 1F according to the present embodiment has the outer appearance configuration and the system configuration that are similar to those of the detection device 1E according to the fourth embodiment.

Also in the present embodiment, the offset adjustment capacity 101 is a variable capacitive element as in the fourth embodiment (the same applies to the sixth to the tenth embodiment described later). In the present embodiment, the offset capacitance value setting unit 121 sets the offset capacitance value to a predefined value (a value determined in advance).

Specifically, in the detection operation (under the detection mode described above), the offset capacitance value setting unit 121 reads the adjustment capacitance value of the predefined value from the memory 124, and switches the offset capacitance value (predefined value) to be an adjustment capacitance value corresponding to each of the detection units 11a to 11d being energized.

In the present embodiment, a plurality of predefined values of the offset adjustment capacity 101 may be set by measuring the capacitance values of the detection units 11a to 11d under a predetermined condition (for example, an environmental condition) determined in advance. The memory 124 stores a plurality of predefined values set in advance. The plurality of predefined values may also be referred to as capacitance candidate values. When the detection device 1F is to be mass produced, a plurality of predefined values may be acquired in advance with a representative sample, to be used as the capacitance candidate value.

When the detection units 11a to 11d have temperature/humidity dependency to have the capacitance value changing depending on the temperature/humidity, the environmental dependency of the capacitance values of the detection units 11a to 11d is detected under an environment with temperature/humidity changing. Thus, based on the result of the detection, the adjustment capacitance value and the gain value described above are determined so as not to overwhelm the range under an environment where the detection device 1F is expected to be used.

Thus, for the A/D converter 105, the detection range is set to be wide considering the temperature/humidity change, for example. Thus, the detection method according to the present embodiment is suitable for detection where a small detection range (in other words, high resolution or high accuracy) is not necessarily required. The detection method according to the present embodiment is suitable for detection for a predetermined detection target and a case where a change in the environment condition is relatively small.

When range over occurs, the detection range of the A/D converter 105 may be switched. This range switching may be automatically performed by the detection control unit 120 when the range over occurs. The detection control unit 120 may notify the user of the occurrence of the range over. In such a case, the user may switch the range manually (through a button operation or the like) in response to the notification.

When the detection range is set to be wider (in other words, when the resolution is set to be lower) as described above, the range is less likely to be overwhelmed, so that the range switching is less likely to be required. Thus, a wide dynamic range can be ensured.

A detection operation performed by the detection device 1F will be described with reference to FIG. 14. FIG. 14 is a flowchart illustrating a procedure for detecting a detection target performed by the detection device 1F. Steps S21 to S22 and S24 to S25 in FIG. 14 are the same processing as that in steps S11 to S12 and S17 to S18 in FIG. 13A, and the detailed descriptions thereof will be omitted. Processing at and around step S23 will be described below.

After step S22, the offset capacitance value setting unit 121 sets the offset capacitance value to be a predefined adjustment capacitance value corresponding to each of the detection units 11a to 11d (step S23). First, the offset capacitance value setting unit 121 sets the offset capacitance value to be a predefined adjustment capacitance value corresponding to the detection unit 11a. Next, the offset capacitance value setting unit 121 sets the offset capacitance value to be a predefined adjustment capacitance value corresponding to the detection unit 11b. Then, the offset capacitance value setting unit 121 sets the offset capacitance value to be a predefined adjustment capacitance value corresponding to the detection unit 11c. Furthermore, the offset capacitance value setting unit 121 sets the offset capacitance value to be a predefined adjustment capacitance value corresponding to the detection unit 11d.

More specifically, in step S23, the offset capacitance value setting unit 121 sets one of the plurality of predefined values stored in the memory 124 to be a predefined adjustment capacitance value corresponding to one of the detection units 11a to 11d. After step S23, the processing proceeds to step S24.

As described above, the detection device 1F includes the detection control unit 120 to set the offset capacitance value to be a predefined value corresponding to each of the detection units 11a to 11d. The detection device 1F uses the predefined value thus set to correct the capacitance value of each of the detection units 11a to 11d.

Here, a case is considered, where at the detection starting point, the detection value of at least some of the detection units 11a to 11d is (i) outside the detectable range or (ii) within the detectable range but is outside the predetermined range set in advance. Such a case is hereinafter referred to as a case where the detection value is excessively large.

The detection device 1F may determine that gas serving as the detection target already exists in a measurement environment, in the case where the detection value is excessively large. The capacitance values of the detection units 11a to 11d have been corrected by using the set predefined values by the detection device 1F, and thus the gas concentration corresponding to a normal detection target is expected to be within the detectable range. Thus, the case where the detection value is excessive large may be regarded as a case where gas has a concentration higher than the excepted level. Alternatively, in the case where the detection value is excessive large, the detection device 1F may determine that at least some of the detection units 11a to 11d are deteriorated.

For example, even when the gain value and the offset adjustment capacity are appropriately set in the manufacturing stage of the detection device 1F, the start-up (power ON) of the detection device 1F under a normal use environment might cause the range to be overwhelmed. In such a case, the detection device 1F determines that (i) gas serving as the detection target already exists in the measurement environment or (ii) at least some of the detection units 11a to 11d are deteriorated. Thus, when the range is overwhelmed immediately after the power is turned ON, the detection device 1F may issue a predetermined error message to the user. Alternatively, the detection device 1F may emit an alarm sound indicating a predetermined error.

As described above, the detection device 1F is suitable for a case where a relatively wide dynamic range is required, but high detection accuracy is not required. Thus, the detection device 1F has a configuration suitable for simple detection. On the other hand, the detection device 1E is suitable for a case requiring high detection accuracy as described above. Thus, a designer of the detection device according to an aspect of the present disclosure may select the configuration of one of the detection devices 1E and 1F, based on the situation of use by the user.

Sixth Embodiment

Hereinafter, a sixth embodiment of the present disclosure will be described with reference to FIG. 6, FIG. 15, and FIG. 16. As illustrated in FIG. 6, a detection device 1G according to the present embodiment has an outer appearance similar to that of the detection device 1B and the like according to the above-described embodiments.

Figure 15:
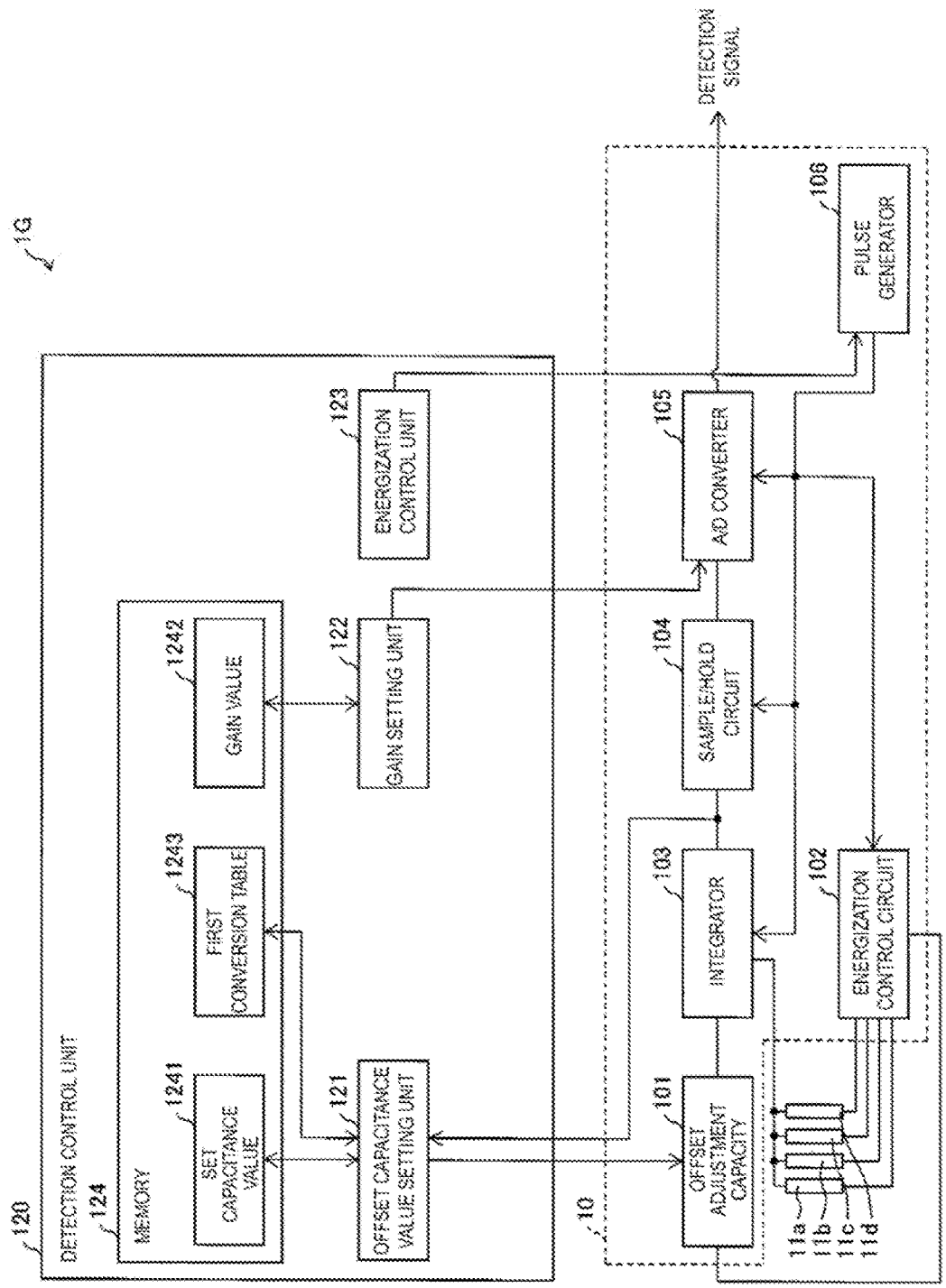
FIG. 15 is a block diagram illustrating a system configuration of the detection device according to the sixth embodiment of the present disclosure.
Figure 16:
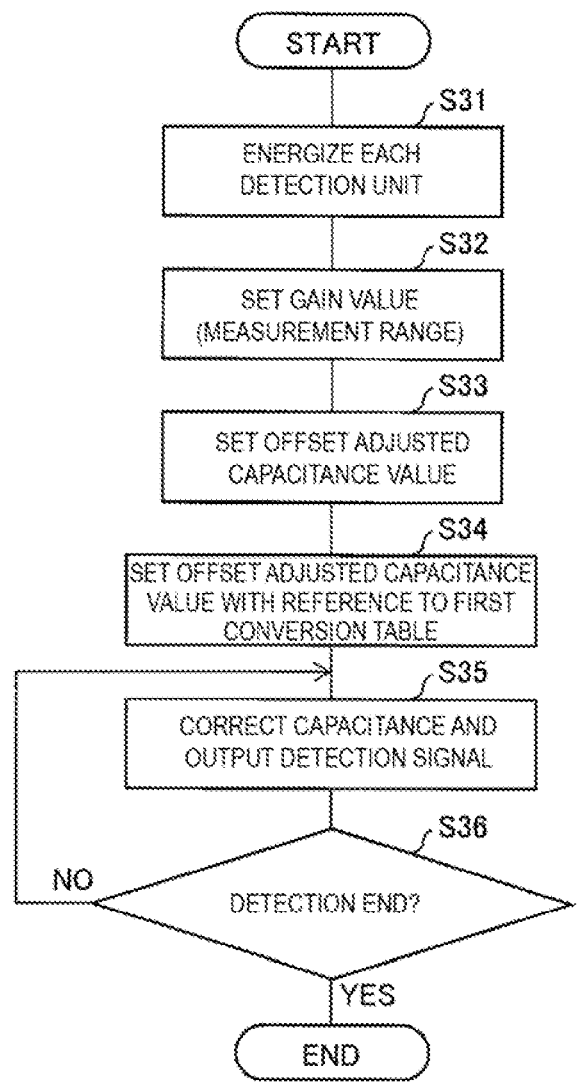
FIG. 16 is a flowchart illustrating a procedure for detecting a detection target performed by the detection device according to the sixth embodiment of the present disclosure.

FIG. 15 is a block diagram illustrating a system configuration of the detection device 1G. As illustrated in FIG. 15, the detection device 1G is obtained by adding a first conversion table 1243 to the memory 124 in the detection device 1E described above. The first conversion table 1243 may be stored in a memory inside or outside the semiconductor circuit 10.

In the present embodiment, any one of the detection units 11a to 11d (for example, the detection unit 11a) is set in advance as a detection unit to be a reference (hereinafter, referred to as a reference detection unit).

The offset capacitance value setting unit 121 corrects a capacitance value set in advance to be a reference (hereinafter, referred to as a reference capacitance value) by using a predetermined conversion equation, to set an offset capacitance value corresponding to the detection units (for example, the detection units 11b to 11d) other than the reference detection unit. The conversion equation takes correction based on a detection environment into consideration. A case where the detection unit 11a is the reference detection unit is described below as an example.

The first conversion table 1243 is prepared in advance for determining the offset capacitance values corresponding to the detection units 11b to 11d, based on the offset capacitance value corresponding to the detection unit 11a. For example, the first conversion table 1243 is generated based on a predetermined conversion equation described later.

The conversion equation can be determined by measuring the capacitance values of the detection units 11a to 11d under an environment with no detection target (gas). For mass produced products, the conversion equation may be determined by using information acquired with a typical sample.

A detection operation performed by the detection device 1G will be described below with reference to FIG. 16. FIG. 16 is a flowchart illustrating a procedure for detecting a detection target performed by the detection device 1G. Steps S31 to S32 and S35 to S36 in FIG. 16 are the same processing as that in steps S11 to S12 and S17 to S18 in FIG. 13A, and the detailed descriptions thereof will be omitted. Processing at and around steps S33 to S34 will be described below.

After step S32, the offset capacitance value setting unit 121 sets the offset capacitance value corresponding to the detection unit 11a (reference detection unit) (step S33). In step S33, the offset capacitance value corresponding to the detection unit 11a is set in a manner similar to that in steps S1001 to S1004 described above. In other words, the offset capacitance value corresponding to the reference detection unit is set highly accurately as in step S13 described above.

Next, the offset capacitance value setting unit 121 sets the offset capacitance values of the respective detection units 11b to 11d, based on the offset capacitance value (offset capacitance value corresponding to the detection unit 11a) set in step S32, by referring to the first conversion table 1243 (step S34). Then, the processing proceeds to step S35.

An example of a conversion equation (correction equation) for generating the first conversion table 1243 will be described below. Here, a case where correction is performed taking the temperature as the detection environment into consideration is described. The temperature may be acquired from a temperature sensor (not illustrated).

Specifically, the conversion equation according to the present embodiment is represented by Equation (1) below.

$$\text{Coffset-}e = \text{Coffset-}0 + a(\text{Tmes} - T0) + b(\text{Cmes1} - C0) \quad (1)$$

This Equation (1) may be referred to as a first conversion equation.

In Equation (1), Coffset-e is a converted offset capacitance value of each of the detection units 11b to 11d other than the reference detection unit (detection unit 11a), a and b are constants, Tmes is peripheral temperature acquired by the temperature sensor, and T0 is a temperature reference value determined in advance.

Cmes1 is a difference value between the capacitance value of the reference detection unit (detection unit 11a) and the offset capacitance value corresponding to the detection unit 11a (set in step S33). In other words, Cmes1 is an output value (actually measured value) of the reference detection unit.

C0 is a capacitance reference value determined in advance for the reference detection unit. Coffset-0 is an offset capacitance value set in advance for each of the detection units 11b to 11d other than the reference detection unit based on the reference condition (T0 and C0).

The values of the constants a and b may be determined based on a result of measurement performed in advance under an environment with no detection target. For example, the values of the constants a and b may be determined by changing the temperature/humidity, measuring an optimum offset capacitance value (a value resulting in an output close to 0) of each of the detection units at each temperature/humidity in advance, and applying a known approximation method to the measurement result.

In the first conversion table 1243, Coffset-e calculated based on Equation (1) described above is set for each of the detection units 11b to 11d other than the reference detection unit (detection unit 11a). Specifically, the values of the constants a and b and Coffset-0 are individually set for each of the detection units 11b to 11d. The values of T0 and C0 may be the same or different among the detection units 11b to 11d.

Coffset-e may be calculated (set) for each of the detection units 11b to 11d not by generating the first conversion table 1243, but by directly performing the calculation based on Equation (1) described above by the offset capacitance value setting unit 121.

Equation (1) described above is an example of the conversion equation and the conversion equation is not limited to this. The conversion equation may be any equation enabling correction based on temperature and the output value from the reference detection unit.

For example, the conversion equation may not necessarily be a linear function for a variable Tmes or Cmes1. In the conversion equation, second- or higher-order terms regarding Tmes or Cmes1 may be included. As the conversion equation, an equation (an equation based on an exponent function, for example) other than polynomials regarding Tmes or Cmes1 may be employed. This applies to the equation (Equation (2), for example) according to a seventh embodiment (described below).

If the output from the reference detection unit is highly responsive mainly to humidity, Cmes1 and C0 may be a value indicating humidity instead of the capacitance value. When Cmes1 is temperature dependent, temperature correction may be performed on Cmes1, and the resultant value of corrected Cmes1 may be used in the conversion equation. This also applies to the equation (Equation (2), for example) according to the seventh embodiment (described below).

Preferably, the detection unit 11a serving as the reference detection unit is preferably highly responsive to humidity (water vapor). This is because with such a detection unit, a baseline can be highly accurately corrected in the detection environment. Furthermore, the detection unit 11a preferably has low responsiveness to a concentration range of the detection target (for example, predetermined gas other than water vapor) compared with its responsiveness to humidity, in the detection environment.

Thus, the detection unit 11a is preferably made of a material having such a property. For example, the detection unit 11a is preferably made of a polymer material featuring excellent hygroscopicity. With the detection unit 11a thus manufactured, the detection unit 11a can function as a humidity sensor.

With this configuration, even when gas of a high concentration serving as the detection target exists in the periphery at the point when the value of Coffset-e (the offset capacitance values of the detection units 11b to 1 d) is set, the value of Coffset-e can be highly accurately set with an influence of the gas reduced.

If the detection unit 11a is highly responsive to humidity, the capacitance change of the detection units 11a to 11d may be measured in advance while changing the humidity of the detection environment, and the conversion equation may be set based on a result of the measurement.

When the semiconductor circuit 10 is provided with a temperature sensor, the first conversion table 1243 may further include a measurement value of the temperature sensor as a variable. Thus, the conversion can be performed with even higher accuracy, based on the temperature.

In such a case, preferably, the capacitance values of the detection units 11a to 11d are measured in advance while changing the temperature as well as humidity in the detection environment, and the conversion equation is set based on a result of the measurement. This is because, generally, responsiveness between the detection material and gas is temperature dependent, that is, becomes high with higher temperature. For another reason, the detection material may be highly temperature dependent against dielectric constant.

With the detection device 1G, the offset capacitance values corresponding to the detection units 11b to 11d can be determined while taking the difference in the response characteristics among the detection units due to the detection environment (in particular, temperature/humidity) into consideration, based on the detection environment and the output from the reference detection unit (detection unit 11a). Thus, the capacitance values of the detection units 11a to 11d can be highly accurately corrected, whereby a detection target at a low concentration can be detected with high resolution with the gain value increased as much as possible.

The detection device 1G does not need to determine the offset capacitance value corresponding to each of the detection units after independently detecting the capacitance value for each of the detection units 11a to 11d, unlike the detection device 1E described above.

A large change in the detection environment (temperature/humidity in particular) in a state where the gain value is large may result in a large change in the output from the reference detection unit (detection unit 11a). Thus, the detection device 1G may determine whether or not the detection environment has changed, based on the output from the detection unit 11a (and the value of the temperature sensor as required). The detection device 1G may reset the offset capacitance value upon detecting a change in the detection environment.

A case is considered where, in the detection device 1G, the range is overwhelmed with a large change in the capacitance values of the other detection units 11b to 11d even with no large change in the output from the reference detection unit (detection unit 11a) or the value of the temperature sensor.

In such a case, the detection device 1G may determine whether the concentration of the detection target (gas) is unexpectedly high, based on the outputs from the detection units 11a to 11d. Upon determining that the concentration of gas is high, the detection device 1G may adjust the gain value to temporarily lower the gain value. With the gain value thus adjusted, highly sensitive detection and a wide dynamic range can both be achieved.

Seventh Embodiment

Hereinafter, a seventh embodiment of the present disclosure will be described with reference to FIG. 6, FIG. 17, and FIG. 18. As illustrated in FIG. 6, a detection device 1H according to the present embodiment has an outer appearance similar to that of the detection device 1B and the like according to the above-described embodiments.

Figure 17:
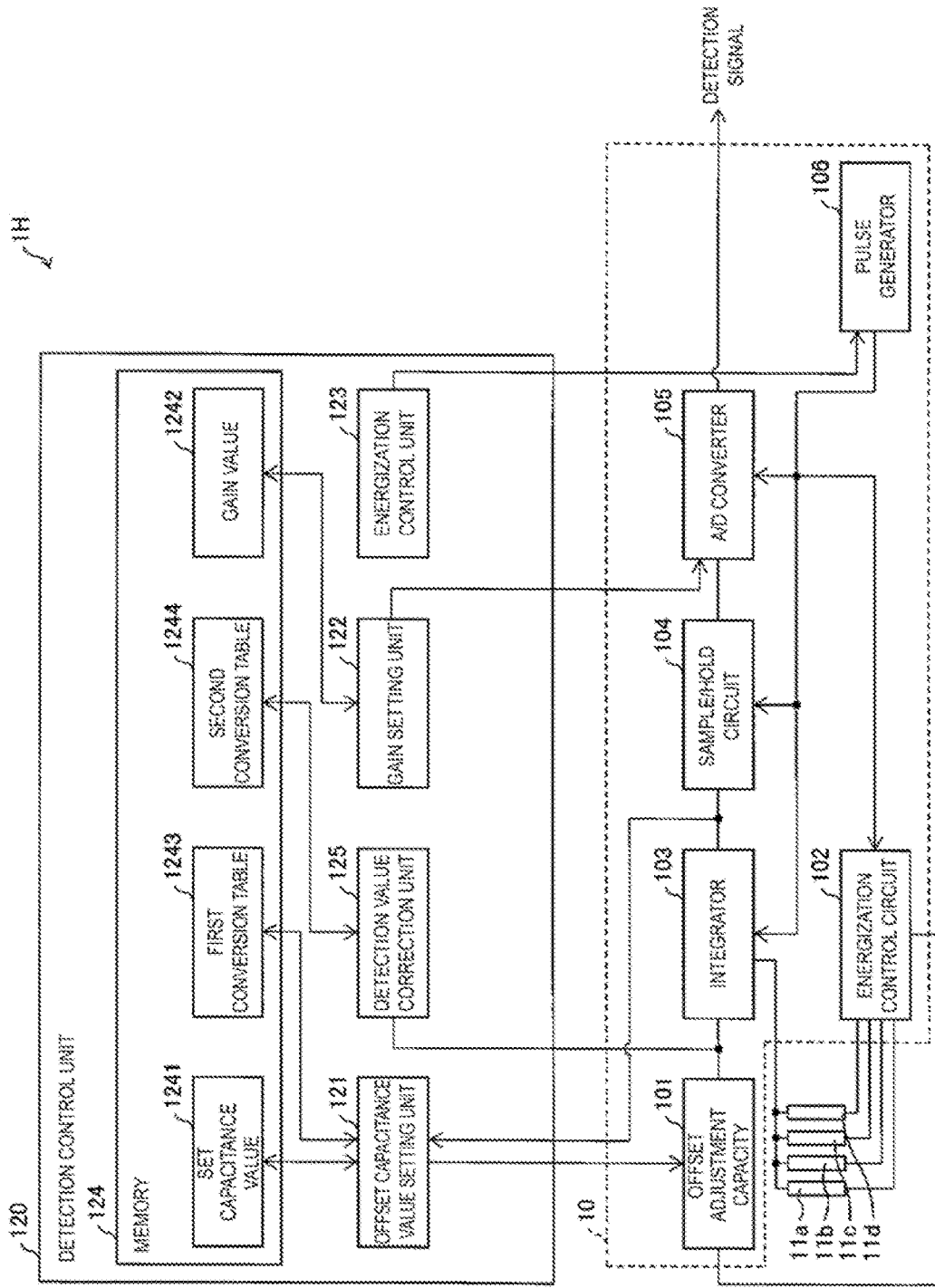
FIG. 17 is a block diagram illustrating a system configuration of the detection device according to the seventh embodiment of the present disclosure.
Figure 18:
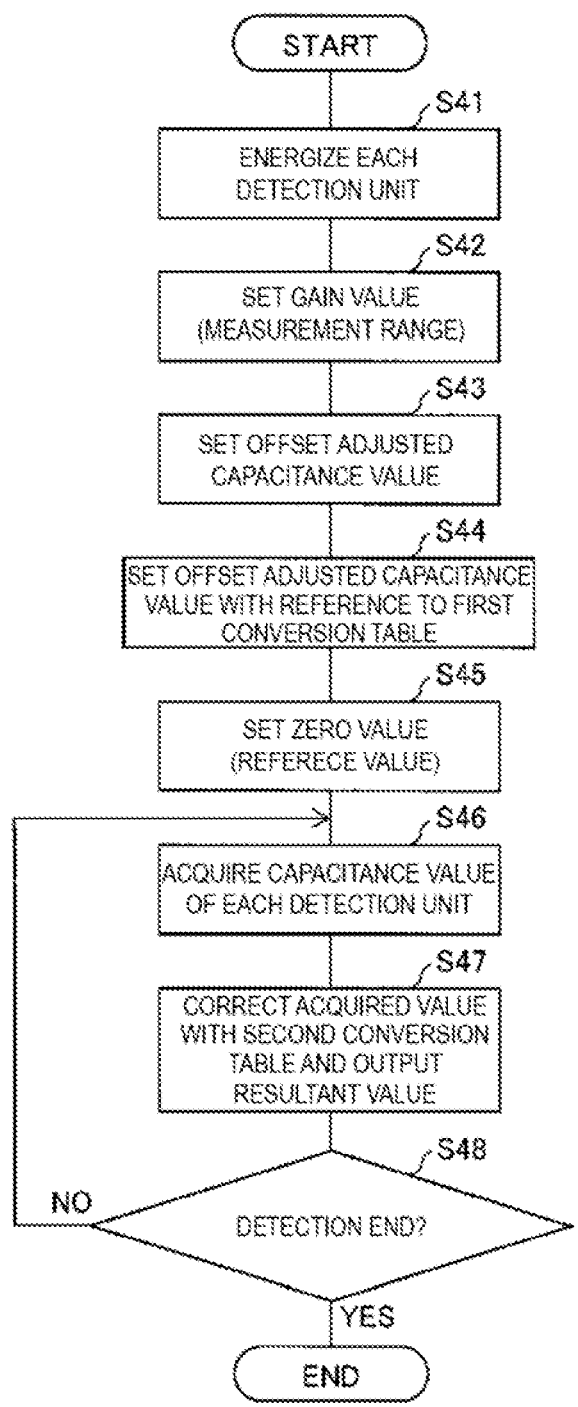
FIG. 18 is a flowchart illustrating a procedure for detecting a detection target performed by the detection device according to the seventh embodiment of the present disclosure.

FIG. 17 is a block diagram illustrating a system configuration of the detection device 1H. As illustrated in FIG. 17, the detection device 1H is obtained by (i) adding a second conversion table 1244 to the memory 124 and (ii) adding a detection value correction unit 125 (difference value correction unit) to the detection control unit 120 in the detection device 1G described above. The second conversion table 1244 may be stored in a memory inside or outside the semiconductor circuit 10.

As described below, the detection value correction unit 125 corrects the difference value (output value) obtained for the other detection units (the detection units 11b to 11d, for example), with the difference value (output value) obtained for a single detection unit (the detection unit 11a, for example) serving as a reference (reference value).

A single detection unit (hereinafter, referred to as an output reference detection unit) serving as a reference of the difference value (output) in the present embodiment may be the same as or different from the reference detection unit in the sixth embodiment described above. Hereinafter, a case in which the detection unit 11a serves as the output reference detection unit will be described.

The second conversion table 1244 is prepared in advance so that the detection value correction unit 125 corrects the output values (a change amount from a zero point) from the other detection units 11b to 11d, with the output value from the detection unit 11a serving as the reference value (for example, the zero point). Note that the reference value does not necessarily need to be limited to the zero point.

For example, the second conversion table 1244 is generated based on a predetermined conversion equation described later. The conversion equation can be determined by measuring the capacitance values of the detection units 11a to 11d in advance under an environment with the detection target (gas) at a predetermined concentration. For mass produced products, the conversion equation may be determined by using information acquired with a typical sample.

A detection operation performed by the detection device 1H will be described below with reference to FIG. 18. FIG. 18 is a flowchart illustrating a procedure for detecting a detection target performed by the detection device 1H. Steps S41 to S44 and S48 in FIG. 18 are the same processing as that in steps S31 to S34 and S36 in FIG. 16 and the detailed descriptions thereof will be omitted. Processing at and around steps S45 to S47 will be described below.

Specifically, in the present embodiment, a method for setting the offset capacitance values respectively corresponding to the detection units 11a to 11d is described to be the same as that in the sixth embodiment described above. Note that the offset capacitance values respectively corresponding to the detection units 11a to 11d may be set with the method according to the fourth or the fifth embodiment described above.

After step S44, the detection value correction unit 125 sets the output value from the detection unit 11a as the reference value (the zero point, for example) (S45). Then, the detection value correction unit 125 acquires the output values (difference values) from the other detection units 11b to 11d (S46). Next, the detection value correction unit 125 corrects the output values from the detection units 11b to 11d based on the reference value set in step S45, by referring to the second conversion table 1244 (S47). Then, the processing proceeds to step S48.

As in the sixth embodiment described above, the detection unit 11a is preferably highly responsive to humidity (water vapor), so that the baseline can be accurately corrected in the environment where the detection element is used. Furthermore, a measurement value obtained by the temperature sensor may be included as a variable in the second table, so that the correction can be performed with particularly high accuracy.

An example of the conversion equation (correction equation) for generating the second conversion table 1244 will be described below. Here, a case where the correction is performed taking the temperature into consideration is described, as in the sixth embodiment described above.

Specifically, the conversion equation according to the present embodiment is represented by Equation (2) below.

$$Cout\text{-}e = Cout \times a2(Tmes-T0) \times b2(Cmes1-C0) \qquad (2)$$

This Equation (2) may be referred to as a second conversion equation.

In Equation (2), Cout-e is an output value (difference value) after the conversion of each of the detection units 11b to 11d other than the output reference detection unit (detection unit 11a), Cout is an actually measured value of the output value (difference value) for each of the detection units 11b to 11d, a2 and b2 are constants, the same as Equation (1) described above applies to Tmes, Cmes1, and C0.

The values of the constants a2 and b2 may be determined based on a result of measurement performed in advance under an environment with a detection target at a certain concentration. For example, the values of the constants a2 and b2 may be determined by changing the temperature/humidity, measuring an output value of each of the detection units at each temperature/humidity in advance, and applying a known approximation method to the measurement result.

If the values of the constants a2 and b2 change in accordance with the concentration of the detection target, the output value from each of the detection units may be measured in advance while changing the concentration. Then, using a result of the measurement, the second conversion table 1244 may be generated by using a conversion equation while further taking the values of the constants a2 and b2 at each concentration into consideration. Thus, the output value can be even more accurately corrected. In such a case, Cout-e is calculated with reference to the second conversion table 1244 based on the three parameters of Cout, Tmes, and Cmes1.

Cout-e calculated with Equation (2) described above is set for each of the detection units 11b to 11d other than the detection unit 11a. Thus, the constants a2 and b2 are individually set to each of the detection units 11b to 11d. The values of T0 and C0 in Equation (2) may be the same or different among the detection units 11b to 11d. The values of T0 and C0 in Equation (2) may be the same or different for the values of T0 and C0 in Equation (1) (conversion equation for generating the first conversion table 1243) described above.

Cout-e may be calculated for each of the detection units 11b to 11d not by generating the second conversion table 1244, but by directly performing the calculation based on Equation (2) described above by the detection value correction unit 125.

Equation (2) described above is an example of the conversion equation and the conversion equation is not limited to this. The conversion equation according to the present embodiment may be any equation with which the correction can be performed based on the output value from the output reference detection unit (detection unit 11a) and the temperature, because of the same reason as that for the conversion equation according to the sixth embodiment described above.

With the detection device 1H, the output values (difference values) from the detection units 11b to 11d can be corrected while taking the difference in the response characteristics among the detection units due to the detection environment (in particular, temperature/humidity) into consideration, based on the detection environment with the output (difference value) from the detection unit 11a serving as a reference. Thus, the capacitance values of the detection units 11a to 11d can be highly accurately corrected, whereby a detection target at a low concentration can be detected with high resolution with the gain value increased as much as possible.

With the detection device 1H, the output value can be corrected with reference to the second conversion table 1244 in addition to the correction (setting) of the offset capacitance value with reference to the first conversion table 1243. As described above, the correction of the offset capacitance value with reference to the first conversion table 1243 reflects the dependency of the capacitance values of the detection units 11a to 11d relative to the temperature/humidity in a state without gas serving as the measurement target.

Thus, in the present embodiment, the output value is corrected with reference to the second conversion table 1244, so that the dependency of the capacitance values of the detection units 11a to 11d against temperature/humidity in the state with the gas can be further taken into consideration. Thus, the detection device 1H can perform the detection with resolution even higher than that of the detection device 1G.

Eighth Embodiment

Hereinafter, a ninth embodiment of the present disclosure will be described with reference to FIG. 6, FIG. 19, and FIG. 20. As illustrated in FIG. 6, a detection device 1J according to the present embodiment has an outer appearance similar to that of the detection device 1B and the like according to the above-described embodiments.

Figure 19:
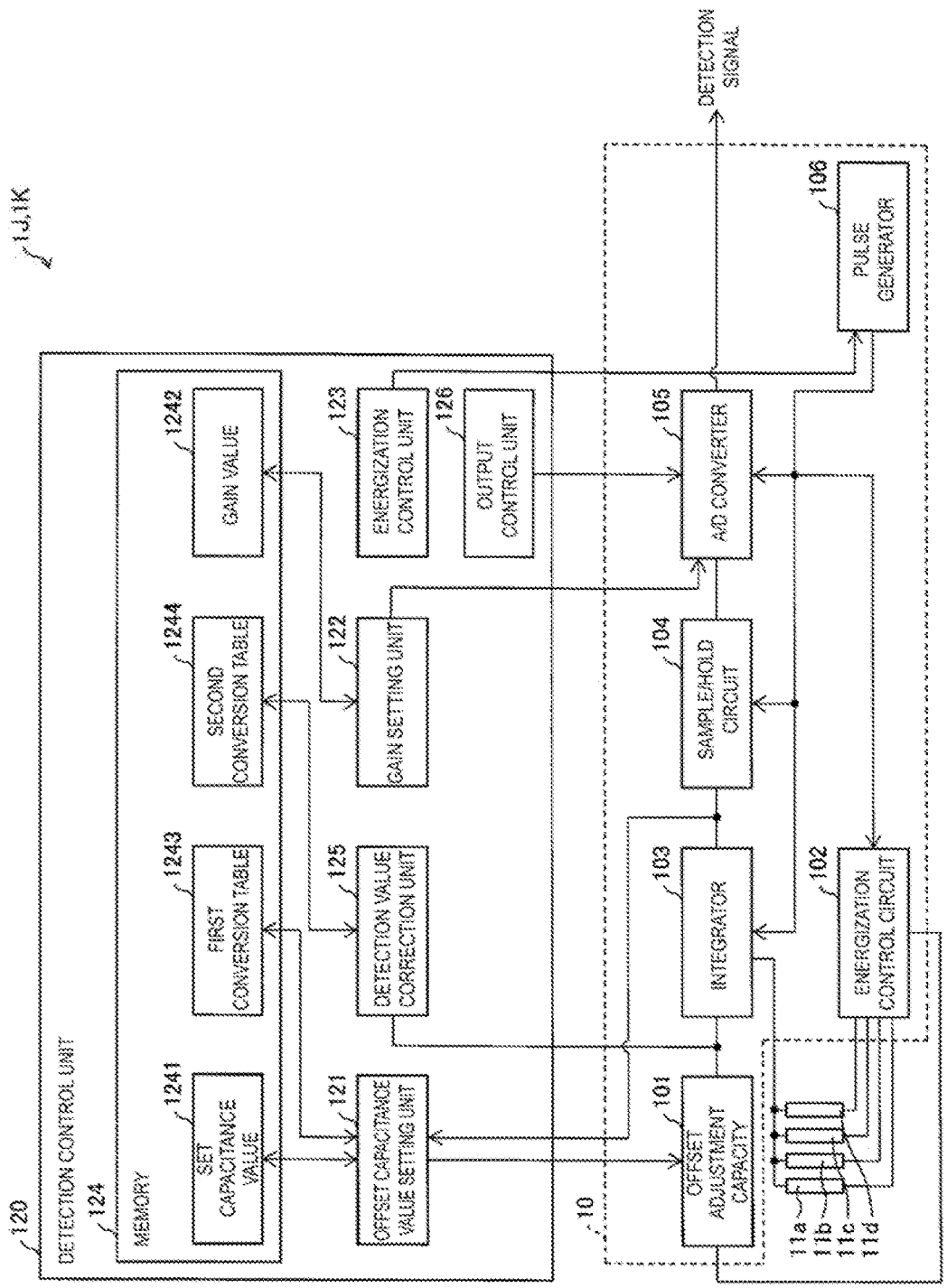
FIG. 19 is a block diagram illustrating a system configuration of the detection device according to the eighth and ninth embodiments of the present disclosure.
Figure 20:
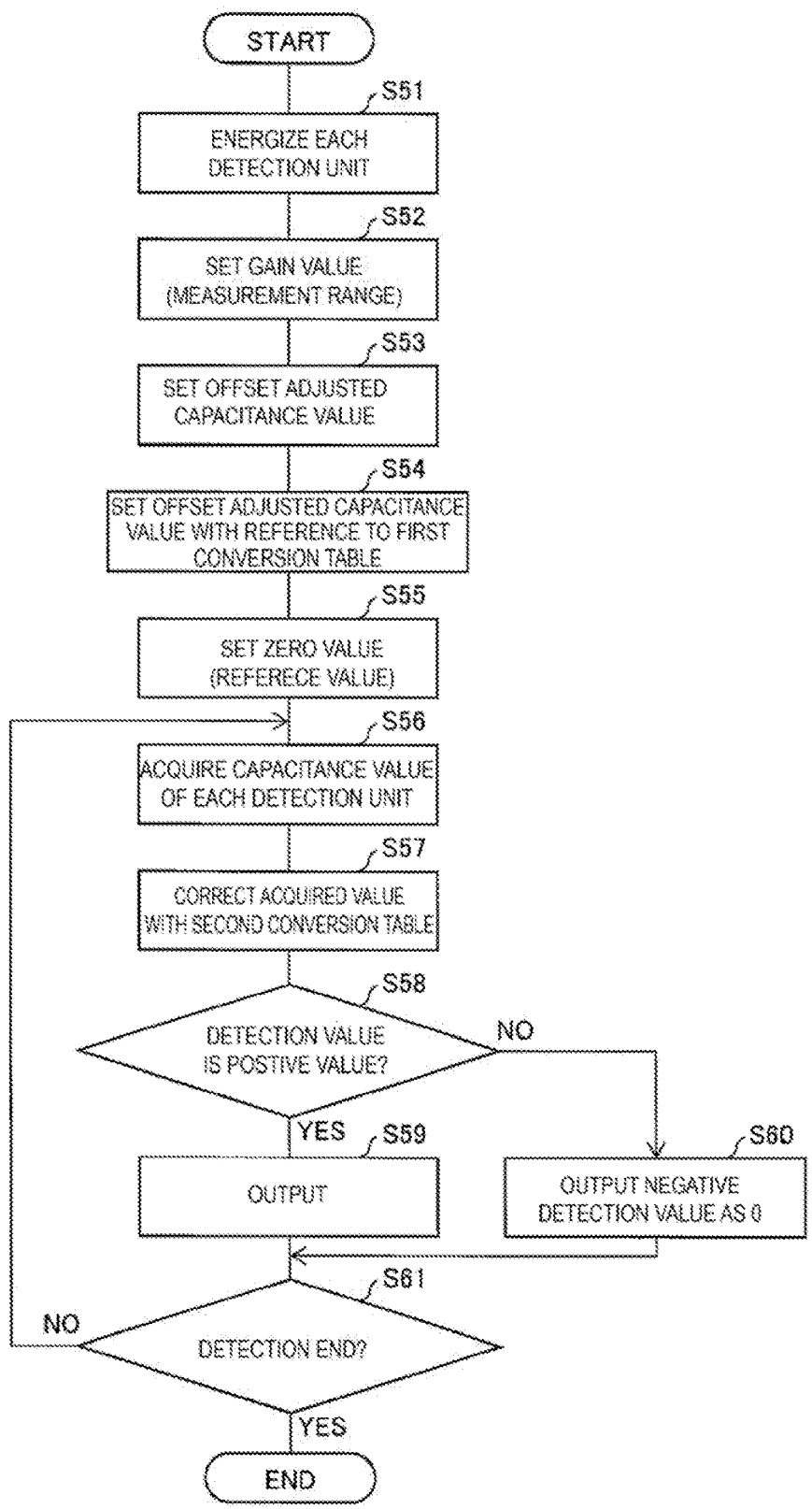
FIG. 20 is a flowchart illustrating a procedure for detecting a detection target performed by the detection device according to the eighth embodiment of the present disclosure.

FIG. 19 is a block diagram illustrating a system configuration of the detection device 1J. As illustrated in FIG. 19, the detection device 1J is obtained by adding an output control unit 126 to the detection control unit 120 in the detection device 1H described above.

As described later, the output control unit 126 instructs the A/D converter 105 to output the difference value (corrected output value) of zero (a zero value), when the output values (difference values) of the detection units 11b to 11d corrected by the detection value correction unit 125 include a negative value.

In the present embodiment, a direction of change in the sign of the output values of the detection units 11b to 11d in a case where the concentration of the gas serving as the detection target increases with the output value (difference value) of the detection unit 11a serving as the reference value (zero point for example) is referred to as a positive side. The direction of change in the sign of the output values of the detection units 11b to 11d in a case where the concentration of the gas decreases is referred to as a negative side.

Generally, the output value (capacitance value) increases/decreases toward the positive side or the negative side in accordance with the type of the detection target, and the direction of the change in the sign regarded as the appropriate detection is referred to as the positive side. This is because, the concentration of gas is represented with a non-negative value, and thus the output value is generally regarded not to be a negative value.

The output value of a negative value may be obtained in a case where the detection material is deteriorated. Even when the detection material has not deteriorated, the output value of a negative value may be obtained if the output value is excessively corrected based on the second conversion table 1244. Thus, in the present embodiment, the output of the A/D converter 105 is controlled so as not to be a negative value (the negative value would be replaced by 0).

A detection operation performed by the detection device 1J will be described below with reference to FIG. 20. FIG. 20 is a flowchart illustrating a procedure for detecting a detection target performed by the detection device 1J. Steps S51 to S57 and S61 in FIG. 20 are the same processing as that in steps S41 to S47 and S48 in FIG. 18 described above and the detailed descriptions thereof will be omitted. Processing at and around steps S58 to S60 will be described below.

After step S57, the output control unit 126 determines whether or not the corrected output values of the detection units 11b to 11d are positive values (S58). When the corrected output values of the detection units 11b to 11d are positive values (YES in S58), the output control unit 126 causes the A/D converter 105 to directly output the corrected output values (S59), and the processing proceeds to S61.

On the other hand, when any of the corrected output values of the detection units 11b to 11d include a negative value (NO in S58), the output control unit 126 instructs the A/D converter 105 to output 0 instead of the negative output value (S60), and the processing proceeds to S61.

The conversion (correction) of the output value with the second conversion table 1244 is performed under an assumption that the output value is a positive value. Thus, the corrected output value of a negative value indicates a failure to appropriately perform the correction based on the second conversion table 1244 (the output value is failed to be sufficiently corrected with the second conversion table 1244). Thus, the detection device 1J does not output an inappropriate correction result (detection result) so that the output value corresponding to the actual detection target concentration can be presented.

The detection device 1J may output an error message instead of outputting the zero value when the negative output value is to be output. Specifically, the detection device 1J may issue any notification that can notify that user that a part of the output values is a negative value (a possibility that the detection result is inappropriate).

Ninth Embodiment

The ninth embodiment of the present disclosure will be described below with reference to FIG. 6, FIG. 19, and FIG. 21. As illustrated in FIG. 6 and FIG. 19 described above, a detection device 1K according to the present embodiment has the outer appearance configuration and the system configuration that are similar to those of the detection device 1J according to the eighth embodiment.

In the present embodiment, the output control unit 126 instructs the A/D converter 105 to output the smallest value of the difference values (corrected output values) as a zero value, when the output values (difference values) from the detection units 11b to 11d corrected by the detection value correction unit 125 include negative values.

A detection operation performed by the detection device 1K will be described below with reference to FIG. 21. FIG. 21 is a flowchart illustrating a procedure for detecting a detection target performed by the detection device 1K. Steps S71 to S79 and S81 in FIG. 21 are the same processing as that in steps S51 to S59 and S61 in FIG. 20 described above and the detailed descriptions thereof will be omitted. Processing at and around step S80 will be described below.

Figure 21:
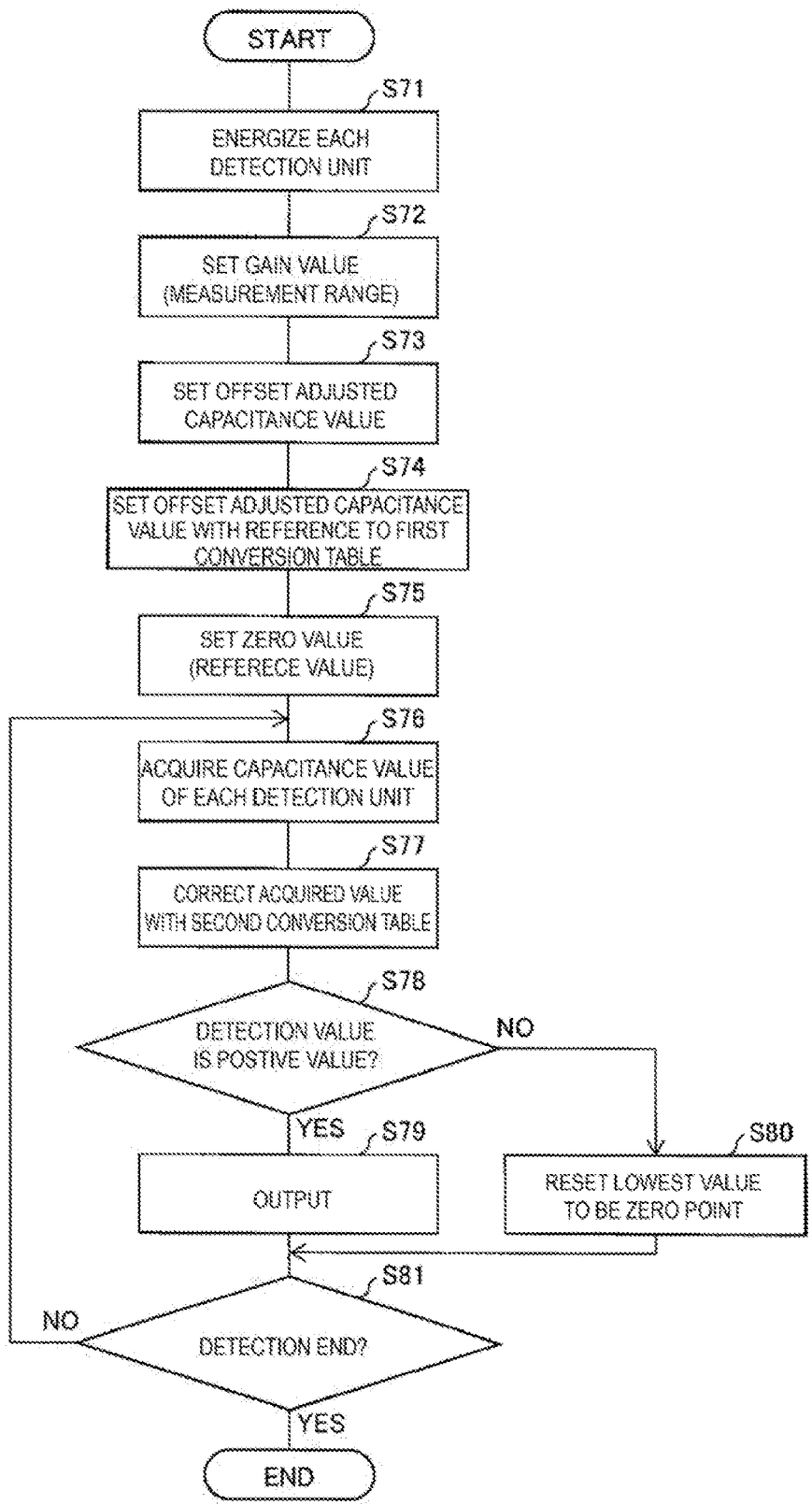
FIG. 21 is a flowchart illustrating a procedure for detecting a detection target performed by the detection device according to the ninth embodiment of the present disclosure.

As illustrated in FIG. 21, when a result of the determination in step S78 indicates that the corrected output values from the detection units 11b to 11d include negative values (NO in S78), the processing proceeds to step S80.

Then, the output control unit 126 instructs the A/D converter 105 to output a smallest value of the negative output values as a zero value (S80). Thus, the output control unit 126 resets the value to the zero value.

With the detection device 1K, the negative output value is reset to the zero value to be eliminated. Thus, the output value can be more appropriately corrected using the second conversion table 1244. Thus, the detection can be performed with higher resolution than that of the detection device 1J.

In the description for the eight and the ninth embodiments, how the change of the output value toward the negative side is addressed is described. The output value (for example, the baseline) may also change toward the positive side. For example, the drift that occurs as a result of a long term use might result not only in the change toward the negative side, but also may result in the change in the positive side. This is because the offset capacitance value adjusted after the power is turned ON (the detection device 1K is started) would not be readjusted until the detection ends.

The change of the baseline toward the positive side is particularly likely to result in erroneous detection of the detection target which does not actually exist. Thus, the detection device 1K preferably also addresses the change in the output value toward the positive value. In the present embodiment, the change in the output value toward the positive side may be addressed by the following method.

For example, output values over a predetermined period may be stored in the memory 124, and when the output value is determined to have not dropped to the zero point (reference value) over the predetermined period based on data on the output values, the detection device 1K may correct the output values so that the smallest value of the positive output values obtained is reset to the zero point (reference value). With this configuration, the output value can be corrected for the change toward both the positive and the negative sides.

Tenth Embodiment

The tenth embodiment of the disclosure will be described with reference to FIG. 6, and FIGS. 22 to 24. As illustrated in FIG. 6, a detection device 1L according to the present embodiment has an outer appearance similar to that of the detection device 1B and the like according to the above-described embodiments.

Figure 22:
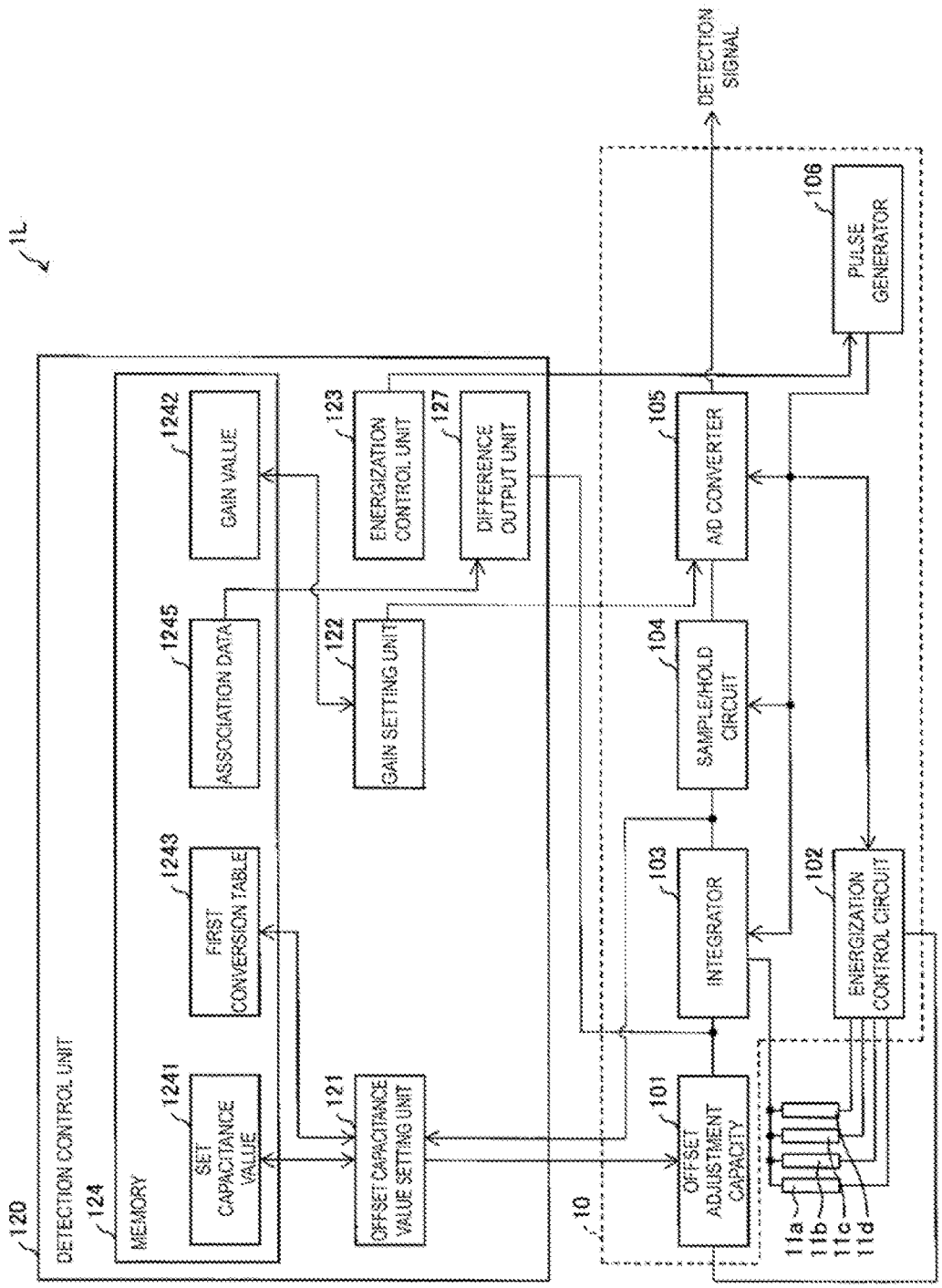
FIG. 22 is a block diagram illustrating a system configuration of the detection device according to the tenth embodiment of the present disclosure.

FIG. 22 is a block diagram illustrating a system configuration of the detection device 1L. As illustrated in FIG. 22, the detection device 1L is obtained by (i) adding a difference output unit 127 (difference calculation unit) to the detection control unit 120 and (ii) adding association data 1245 to the memory 124, in the detection device 1G described above. The association data 1245 may be stored in a memory inside or outside the semiconductor circuit 10.

Figure 23:
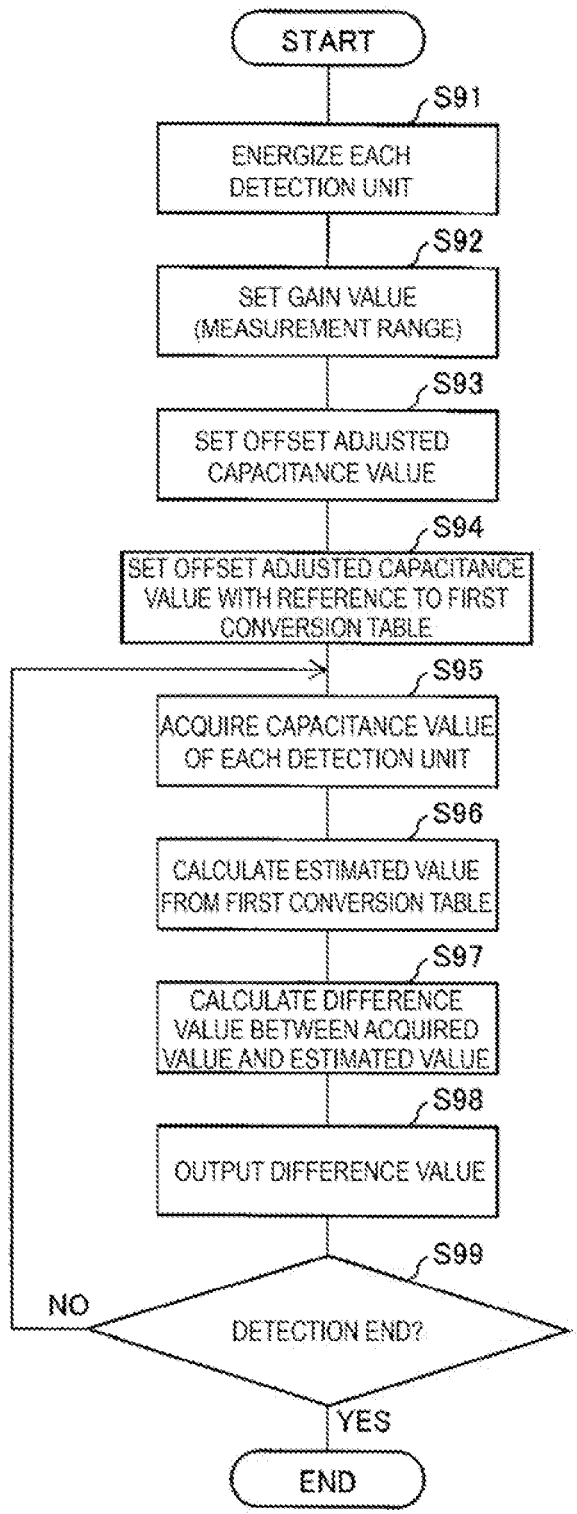
FIG. 23 is a flowchart illustrating a procedure for detecting a detection target performed by the detection device according to the tenth embodiment of the present disclosure.

A detection operation performed by the detection device 1L will be described below with reference to FIG. 23. FIG. 23 is a flowchart illustrating a procedure for detecting a detection target performed by the detection device 1K. Steps S91 to S94 and S99 in FIG. 23 are the same processing as that in steps S31 to S34 and S36 in FIG. 16 and the detailed descriptions thereof will be omitted. Processing at and around steps S95 to S98 will be described below.

After step S94, the corrected output value of the respective detection units 11b to 11d other than the detection unit 11a (reference detection unit) are input to the detection control unit 120 (S95).

In the present embodiment, estimated value from the detection units 11b to 11d (also referred to as estimated output values or estimated difference values) in a state where there is no detection target (gas) is in the measurement environment are stored in the memory 124 in association with the first conversion table 1243 and the output value from the reference detection unit (detection unit 11a). The association data 1245 data (more specifically, a table) indicates the association.

Specifically, in the association data 1245, the estimated output value is stored in the memory 124 in association with the first conversion table 1243. The estimated output value indicates an output value that is supposed to be output when the measurement starts with the offset capacitance value set with reference to the first conversion table 1243 under a normal condition (a state without the gas).

Next, the difference output unit 127 acquires the association data 1245 (estimated output value) from the memory 124 (S96), and calculates the difference value between the estimated output value (estimated value) and the output values of the detection units 11b to 11d (actually measured value (also referred to as an acquired value or an acquired difference value)) based on the association data 1245 (S97). Next, the difference output unit 127 outputs the difference value (S98). Then, the processing proceeds to S99.

With this configuration, when gas at high concentration exists in the periphery of the detection device 1L at the point when the offset capacitance value is set, a large difference value between the output value (actually measured value) of the detection units 11b to 11d and the estimated output value is obtained. Thus, the amount of gas existing in the initial state can be identified based on the difference value. Thus, the detection can be performed while taking the amount of the gas into consideration.

In the present embodiment, when the difference value of a negative value is obtained (that is when the estimated output value is larger than the actual output value), the processing that is similar to those in the eighth and the ninth embodiments may be executed. This is because such a value indicates a possibility of a failure to appropriately perform the detection or correction.

The correction based on the second conversion table 1244 may be further executed on the difference value calculated in step S98.

Modified Example

Figure 24:
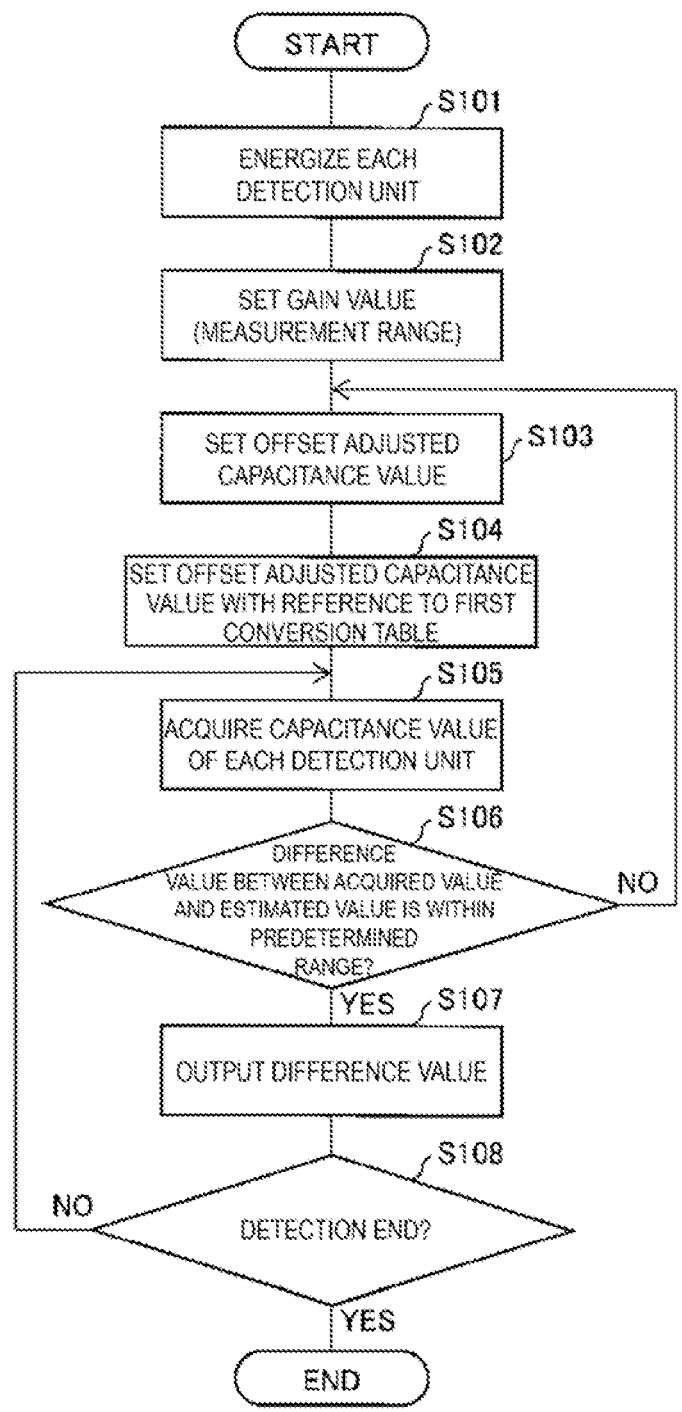
FIG. 24 is a flowchart illustrating a procedure for detecting a detection target performed by a detection device according to a modified example of the tenth embodiment.

FIG. 24 is a flowchart illustrating a procedure for detecting a detection target performed by the detection device 1L. Steps S101 to S105 and S107 and S108 in FIG. 24 are the same processing as that in steps S91 to S95 and S98 and S99 in FIG. 23 described above and the detailed descriptions thereof will be omitted. Processing at and around step S106 will be described below.

In the present modified example, the difference output unit 127 determines whether the difference value between the estimated value and the actually measured value is within a predetermined range set in advance (S106). When the difference value exceeds the predetermined range (NO in S106), the processing returns to S103. Thus, the offset capacitance value setting is repeated until the difference value falls within the predetermined range (YES in S106).

A relatively large difference value indicates that gas at a high concentration is expected to be in the periphery of the detection device 1K in the initial state to affect the reference value of the reference detection unit (detection unit 11a).

In view of this, in the processing described above, the existence of the gas at a high concentration in the initial state is detected and the offset capacitance value is reset in accordance with the gas concentration. With this processing, the output value can be suitably corrected even when gas at a high concentration exists in the initial state.

The detection device 1L may output an error message when the difference value exceeds the predetermined range. Thus, the detection device 1L may instruct the user to perform the detection again in a normal environment (a state where the gas concentration is relatively low) because the gas at a high concentration exists in the initial state (because the measurement environment is abnormal).

When the difference value exceeds the predetermined range, the detection device 1L may cause the processing to wait until the difference value exceeds the predetermined range instead of returning to S103. In other words, the offset adjustment capacity may be reset when the difference value falls within the predetermined range. Also with this processing, the output value can be favorably corrected.

Implementation Example by Software

A control block (in particular, the detection unit 120) of the detections devices 1, 1A to 1H, and 1J to 1L may be realized by a logic circuit (hardware) formed in an integrated circuit (IC chip) and the like, or by software by using Central Processing Unit (CPU).

In the latter case, the detections devices 1, 1A to 1H, and 1J to 1L include CPU configured to execute a command of a program, that is software, to realize each function, Read Only Memory (ROM) or a storage device (these are referred to as "recording medium") configured to store the program and various types of data in a manner capable of being read by a computer (or CPU), Random Access Memory (RAM) to develop the program, and the like. Then, the computer (or CPU) reads the program from the recording medium and executes the program to achieve the object of the present disclosure. As the recording medium, a "non-transitory tangible medium", such as a tape, a disk, a card, a semiconductor memory, and a programmable logic circuit may be used. Further, the program may be supplied to the computer via any transmission medium (a communication network, a broadcast wave, or the like) able to transmit the program. Note that the present disclosure may be implemented in a form of data signal embedded in a carrier wave, which is embodied by electronic transmission of the program.

ADDITIONAL NOTES

The present disclosure is not limited to each of the above-described embodiments. It is possible to make various modifications within the scope of the claims. An embodiment obtained by appropriately combining technical elements each disclosed in different embodiments falls also within the technical scope of the present disclosure. Furthermore, technical elements disclosed in the respective embodiments may be combined to provide a new technical feature.

CROSS-REFERENCE TO RELATED APPLICATIONS

This application claims the benefit of priority to Japanese Patent Application Number 2016-144914, filed on Jul. 22, 2016. The entire contents of the above-identified application are hereby incorporated by reference.

REFERENCE SIGNS LIST 1, 1A to 1H, 1J to 1L Detection device
10, 10A, 10B Semiconductor circuit
11, 11a to 11d Detection unit
12, 12A, 12B Substrate
13, 13A, 13B Conductive wiring line
101 Offset adjustment capacity (correction capacitive element)
103 Integrator (difference acquisition circuit)
105 A/D converter (conversion circuit)
111 Detection layer
121 Offset capacitance value setting unit (capacitance value setting unit)
125 Detection value correction unit (difference value correction unit)
126 Output control unit
127 Difference output unit (difference calculation unit)

The invention claimed is:
1. A detection device comprising:
a plurality of detection units each formed on a semiconductor circuit and including a detection layer that includes a material whose capacitance value varying when the material comes into contact with a detection target;
a correction capacitive element that indicates a correction capacitance value for correcting detected capacitance values detected by the detection units;

a difference acquisition circuit that acquires a difference value between each of the detected capacitance values and the correction capacitance value; and a conversion circuit that converts the difference value into a digital signal, wherein the correction capacitive element, the difference acquisition circuit, and the conversion circuit are formed on the semiconductor circuit, the plurality of detection units include a first detection unit including a first detection layer and a second detection unit including a second detection layer, the first and second detection units being different from each other, and the first detection layer in the first detection unit and the second detection layer in the second detection unit are made of different materials.

2. The detection device according to claim 1, wherein the semiconductor circuit comprises a plurality of semiconductor circuits.

3. The detection device according to claim 1, further comprising a substrate provided separately from the semiconductor circuit, wherein at least one of the detection units is formed on the substrate and is connected to the semiconductor circuit via a conductive wiring line.

4. The detection device according to claim 1, wherein the first detection layer in the first detection unit and the second detection layer in the second detection unit are formed to have thicknesses with which the capacitance values of the first detection unit and the second detection unit fall within a predetermined range.

5. A detection device comprising:

a plurality of detection units each formed on a semiconductor circuit and including a detection layer that includes a material whose capacitance value varying when the material comes into contact with a detection target;

a correction capacitive element that indicates a correction capacitance value for correcting detected capacitance values detected by the detection units;

a difference acquisition circuit that acquires a difference value between each of the detected capacitance values and the correction capacitance value; and a conversion circuit that converts the difference value into a digital signal, wherein the correction capacitive element, the difference acquisition circuit, and the conversion circuit are formed on the semiconductor circuit, the correction capacitive element is a variable capacitive element the correction capacitance value of which is variable, and the detection device further includes a capacitance value setting unit that sets the correction capacitance value in accordance with the difference values obtained by the difference acquisition circuit.

6. The detection device according to claim 1, wherein the correction capacitive element is a variable capacitive element the correction capacitance value of which is variable, and the detection device further includes a capacitance value setting unit that sets the correction capacitance value to be a predetermined value.

7. The detection device according to claim 5, wherein one of the plurality of detection units to serve as a reference is used as a reference detection unit, and the capacitance value setting unit sets the correction capacitance value by using a first conversion equation based on a detection environment, for the detection units other than the reference detection unit.

8. The detection device according to claim 7, further comprising a difference value correction unit that uses the difference value obtained for one of the detection units as a reference and corrects the difference values obtained for the other detection units by using a second conversion equation based on the detection environment.

9. The detection device according to claim 8, further comprising an output control unit that outputs, when the difference values corrected by the difference value correction unit include a difference value of a negative value, the difference value as zero.

10. The detection device according to claim 8, further comprising an output control unit that sets and outputs, when the difference values corrected by the difference value correction unit include difference values of negative values, a smallest value of the difference values as a zero value.

11. The detection device according to claim 8, further comprising a difference calculation unit that calculates, based on an association between an estimated difference value that is an estimated value of the difference value in a state where a detection environment does not include the detection target and an acquired difference value that is supposed to be acquired by the difference acquisition circuit, a difference between the difference value acquired by the difference acquisition circuit and the estimated difference value corresponding to the acquired difference value.

12. The detection device according to claim 11, wherein when a difference between the estimated difference value and the acquired difference value exceeds a predetermined range, the capacitance value setting unit continues to set the correction capacitance value until the difference falls within the predetermined range.

13. A method of controlling a detection device including:

a semiconductor circuit;

a plurality of detection units each formed on the semiconductor circuit and including a detection layer that includes a material whose capacitance value varying when the material comes into contact with a detection target;

a correction capacitive element;

a difference acquisition circuit; and a conversion circuit, the correction capacitive element, the difference acquisition circuit, and the conversion circuit being formed on the semiconductor circuit, the method of controlling the detection device comprising:

a step of the difference acquisition circuit acquiring difference values between detected capacitance values detected by the detection units and a correction capacitance value indicated by the correction capacitive element to correct the detected capacitance values;

a step of the conversion circuit converting the difference values to digital signals; and a capacitance value setting step of setting the correction capacitance value in accordance with the difference values obtained by the difference acquisition circuit.

* * * * *